(12) United States Patent
Felix et al.

(10) Patent No.: US 11,696,681 B2
(45) Date of Patent: Jul. 11, 2023

(54) CONFIGURABLE HARDWARE PLATFORM FOR PHYSIOLOGICAL MONITORING OF A LIVING BODY

(71) Applicant: Bardy Diagnostics, Inc., Seattle, WA (US)

(72) Inventors: Jason Felix, Vashon Island, WA (US); Joshua Djon Green, Seattle, WA (US); Corey B. Williamson, Bellingham, WA (US); Gust H. Bardy, Carnation, WA (US)

(73) Assignee: Bardy Diagnostics Inc., Bellevue, WA (US)

( * ) Notice: Subject to any disclaimer, the term of this patent is extended or adjusted under 35 U.S.C. 154(b) by 0 days.

(21) Appl. No.: 16/929,390

(22) Filed: Jul. 15, 2020

(65) Prior Publication Data

US 2021/0000345 A1 Jan. 7, 2021

Related U.S. Application Data

(63) Continuation-in-part of application No. 16/926,381, filed on Jul. 10, 2020, now Pat. No. 11,096,579,
(Continued)

(51) Int. Cl.
*A61B 5/00* (2006.01)
*H04Q 9/02* (2006.01)
(Continued)

(52) U.S. Cl.
CPC .......... *A61B 5/0006* (2013.01); *A61B 5/0022* (2013.01); *A61B 5/0031* (2013.01);
(Continued)

(58) Field of Classification Search
CPC combination set(s) only.
See application file for complete search history.

(56) References Cited

U.S. PATENT DOCUMENTS 3,215,136 A 11/1965 Holter et al.
3,569,852 A 3/1971 Berkovits
(Continued)

FOREIGN PATENT DOCUMENTS

WO 2010104952 9/2010
WO 2012040487 3/2012
WO 2012112407 8/2012

OTHER PUBLICATIONS

Dwayne C. Leonard, A Framework for the Creation of a Unified Electronic Medical Record Using Biometrics, Data Fusion and Belief Theory, 2007, https://dialog.proquest.com/professional/docview/304852676/17AEEF1F9382EF1C4E5/6?accountid=131444 (last visited Aig 27, 2021) (Year: 2007).
(Continued)

*Primary Examiner* — Nathan J Jenness
*Assistant Examiner* — Michael A Catina
(74) *Attorney, Agent, or Firm* — Leonid Kisselev

(57) ABSTRACT

An implantable medical device is disclosed. A housing includes a hollow body forming a first electrode on an outer surface with end caps affixed to opposite ends, one end cap forming a second electrode. A microcontroller circuit is provided and includes a microcontroller operable under program instructions stored within a non-volatile memory device. An analog front end is interfaced to the electrodes to sense electrocardiographic signals. A transceiver circuit is operable to wirelessly communicate with an external data device. The program instructions define instructions to continuously sample the electrocardiographic signals into the non-volatile memory device and to offload the non-volatile memory device to the external data device. A receiving coil and a charging circuit are operable to charge an onboard power source for the microcontroller circuit.

17 Claims, 8 Drawing Sheets

Related U.S. Application Data which is a continuation-in-part of application No. 16/919,626, filed on Jul. 2, 2020, now Pat. No. 11,116,451.

(60) Provisional application No. 62/962,773, filed on Jan. 17, 2020, provisional application No. 62/874,086, filed on Jul. 15, 2019, provisional application No. 62/873,740, filed on Jul. 12, 2019, provisional application No. 62/873,754, filed on Jul. 12, 2019, provisional application No. 62/870,506, filed on Jul. 3, 2019.

(51) Int. Cl.

| | | |
|---|---|---|
| *A61B 5/07* | (2006.01) | |
| *A61B 5/0205* | (2006.01) | |
| *A61B 5/287* | (2021.01) | |
| *H04L 12/28* | (2006.01) | |
| *G16H 50/20* | (2018.01) | |
| *G16H 80/00* | (2018.01) | |
| *G16H 40/67* | (2018.01) | |
| *A61B 5/1455* | (2006.01) | |
| *A61B 5/021* | (2006.01) | |
| *A61B 5/08* | (2006.01) | |
| *A61B 5/087* | (2006.01) | |
| *A61B 5/145* | (2006.01) | |

(52) U.S. Cl.
CPC .......... *A61B 5/02055* (2013.01); *A61B 5/073* (2013.01); *A61B 5/287* (2021.01); *G16H 40/67* (2018.01); *G16H 50/20* (2018.01); *G16H 80/00* (2018.01); *H04L 12/2825* (2013.01); *H04Q 9/02* (2013.01); *A61B 5/021* (2013.01); *A61B 5/087* (2013.01); *A61B 5/0816* (2013.01); *A61B 5/14532* (2013.01); *A61B 5/14552* (2013.01); *A61B 2560/0219* (2013.01); *A61B 2562/0219* (2013.01); *H04Q 2209/886* (2013.01)

(56) References Cited

U.S. PATENT DOCUMENTS

| | | |
|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,506,678 A | 3/1985 | Russell et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,788,983 A | 12/1988 | Brink et al. |
| 4,809,705 A | 3/1989 | Ascher |
| 4,915,656 A | 4/1990 | Alferness |
| 5,007,429 A | 4/1991 | Treatch et al. |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,312,446 A | 5/1994 | Holschbach et al. |
| 5,314,453 A | 5/1994 | Jeutter |
| 5,331,966 A | 7/1994 | Bennett et al. |
| 5,333,615 A | 8/1994 | Craelius et al. |
| 5,341,806 A | 8/1994 | Gadsby et al. |
| 5,348,008 A | 9/1994 | Bomn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,479,922 A | 1/1996 | Reichl |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| 5,860,918 A | 1/1999 | Schradi |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,956,013 A | 9/1999 | Raj et al. |
| 5,957,857 A | 9/1999 | Hartley |
| 5,984,102 A | 11/1999 | Tay |
| 5,987,352 A * | 11/1999 | Klein .................. A61N 1/08 600/509 |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,185,452 B1 * | 2/2001 | Schulman ............ A61B 5/0031 604/20 |
| 6,188,407 B1 | 2/2001 | Smith et al. |
| 6,190,350 B1 | 2/2001 | Davis et al. |
| D443,063 S | 5/2001 | Pisani et al. |
| 6,245,025 B1 | 6/2001 | Torok et al. |
| 6,246,330 B1 | 6/2001 | Nielsen |
| 6,249,696 B1 | 6/2001 | Olson et al. |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,434,410 B1 | 8/2002 | Cordero |
| 6,454,708 B1 | 9/2002 | Ferguson et al. |

(56) References Cited

U.S. PATENT DOCUMENTS

| | | |
|---|---|---|
| 6,456,256 B1 | 9/2002 | Amundson et al. |
| 6,456,872 B1 | 9/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |
| 6,887,201 B2 | 5/2005 | Bardy |
| 6,893,397 B2 | 5/2005 | Bardy |
| 6,895,261 B1 | 5/2005 | Palamides |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,052,472 B1 | 5/2006 | Miller et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,672,714 B2 | 3/2010 | Kuo et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegel et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,545,416 B1 | 10/2013 | Kayyali et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,858,432 B2 * | 10/2014 | Robertson ............ A61B 5/0031 600/300 |
| 8,938,287 B2 | 1/2015 | Felix et al. |
| 8,948,935 B1 | 2/2015 | Peeters |
| 8,965,492 B2 | 2/2015 | Baker et al. |
| 9,066,664 B2 | 6/2015 | Karjalainen |
| 9,135,608 B2 | 9/2015 | Herlitz |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,597,004 B2 | 3/2017 | Hughes et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 10,548,632 B2 | 2/2020 | Sick et al. |
| 2001/0051766 A1 * | 12/2001 | Gazdzinski ............ A61B 10/02 606/1 |
| 2002/0013538 A1 | 1/2002 | Teller |
| 2002/0013717 A1 | 1/2002 | Ando et al. |
| 2002/0016798 A1 | 2/2002 | Sakai |
| 2002/0082867 A1 | 6/2002 | MacCarter et al. |
| 2002/0103422 A1 | 8/2002 | Harder et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0149349 A1 | 8/2003 | Jensen |
| 2003/0174881 A1 | 9/2003 | Simard et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |

(56) References Cited

U.S. PATENT DOCUMENTS

| | | |
|---|---|---|
| 2004/0049120 A1 | 3/2004 | Cao et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0199140 A1 | 10/2004 | Rue et al. |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0043640 A1 | 2/2005 | Chang |
| 2005/0058701 A1* | 3/2005 | Gross ............... A61K 9/0097 374/E13.002 |
| 2005/0096717 A1 | 5/2005 | Bishay et al. |
| 2005/0101875 A1 | 5/2005 | Semler et al. |
| 2005/0108055 A1 | 5/2005 | Ott et al. |
| 2005/0113661 A1 | 5/2005 | Nazeri |
| 2005/0137485 A1 | 6/2005 | Cao et al. |
| 2005/0151640 A1 | 7/2005 | Hastings |
| 2005/0154267 A1 | 7/2005 | Bardy |
| 2005/0154294 A1* | 7/2005 | Uchiyama ............ A61B 1/0676 600/420 |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030781 A1 | 2/2006 | Shennib |
| 2006/0030904 A1 | 2/2006 | Quiles |
| 2006/0041201 A1 | 2/2006 | Behbehani et al. |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0111943 A1 | 5/2006 | Wu |
| 2006/0122469 A1 | 6/2006 | Martel |
| 2006/0124193 A1 | 6/2006 | Orr et al. |
| 2006/0167502 A1 | 7/2006 | Haefner |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0088419 A1 | 4/2007 | Fiorina et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0142722 A1 | 6/2007 | Chang |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0233198 A1 | 10/2007 | Ghanem et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0270678 A1 | 11/2007 | Fadem |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0027337 A1 | 1/2008 | Dugan |
| 2008/0027339 A1 | 1/2008 | Nagai et al. |
| 2008/0051668 A1 | 2/2008 | Bardy |
| 2008/0058661 A1 | 3/2008 | Bardy |
| 2008/0143080 A1 | 3/2008 | Burr |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0243012 A1 | 10/2008 | Fujihashi et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0309481 A1 | 12/2008 | Tanaka et al. |
| 2008/0312522 A1 | 12/2008 | Rowlandson et al. |
| 2009/0009342 A1 | 1/2009 | Karjalainen |
| 2009/0012412 A1 | 1/2009 | Wiesel |
| 2009/0012979 A1 | 1/2009 | Bateni et al. |
| 2009/0054737 A1 | 2/2009 | Magar et al. |
| 2009/0054952 A1 | 2/2009 | Glukhovsky et al. |
| 2009/0062670 A1 | 3/2009 | Sterling |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0076364 A1 | 4/2009 | Libbus et al. |
| 2009/0088652 A1 | 4/2009 | Tremblay |
| 2009/0093687 A1 | 4/2009 | Telfort et al. |
| 2009/0112116 A1 | 4/2009 | Lee et al. |
| 2009/0131759 A1 | 5/2009 | Sims et al. |
| 2009/0133047 A1 | 5/2009 | Lee et al. |
| 2009/0156908 A1 | 6/2009 | Belalcazar et al. |
| 2009/0182204 A1 | 7/2009 | Semler et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2009/0327715 A1 | 12/2009 | Smith et al. |
| 2010/0007413 A1 | 1/2010 | Herleikson et al. |
| 2010/0022863 A1 | 1/2010 | Mogensen et al. |
| 2010/0022897 A1 | 1/2010 | Parker et al. |
| 2010/0056877 A1 | 3/2010 | Fein et al. |
| 2010/0056881 A1 | 3/2010 | Libbus et al. |

(56) References Cited

U.S. PATENT DOCUMENTS

| | | |
|---|---|---|
| 2010/0076517 A1 | 3/2010 | Imran |
| 2010/0081913 A1 | 4/2010 | Cross et al. |
| 2010/0137694 A1 | 6/2010 | Irazoqui et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234697 A1 | 9/2010 | Walter et al. |
| 2010/0234715 A1 | 9/2010 | Shin et al. |
| 2010/0234716 A1 | 9/2010 | Engel |
| 2010/0268103 A1 | 10/2010 | McNamara et al. |
| 2010/0280366 A1 | 11/2010 | Arne et al. |
| 2010/0298720 A1 | 11/2010 | Potkay |
| 2010/0312188 A1 | 12/2010 | Robertson et al. |
| 2010/0317957 A1 | 12/2010 | Lee et al. |
| 2010/0324384 A1 | 12/2010 | Moon et al. |
| 2010/0324405 A1 | 12/2010 | Niemi et al. |
| 2011/0021937 A1 | 1/2011 | Hugh et al. |
| 2011/0041613 A1 | 2/2011 | Tran et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0082842 A1 | 4/2011 | Groseclose, Jr. et al. |
| 2011/0105861 A1 | 5/2011 | Derchak et al. |
| 2011/0112379 A1 | 5/2011 | Li et al. |
| 2011/0144470 A1 | 6/2011 | Mazar et al. |
| 2011/0160548 A1 | 6/2011 | Forster |
| 2011/0160601 A1 | 6/2011 | Wang et al. |
| 2011/0208076 A1 | 8/2011 | Fong et al. |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1 | 11/2011 | Kaib et al. |
| 2011/0313305 A1 | 12/2011 | Rantala |
| 2012/0003933 A1 | 1/2012 | Baker et al. |
| 2012/0029300 A1 | 2/2012 | Paquet |
| 2012/0029306 A1 | 2/2012 | Paquet et al. |
| 2012/0029309 A1 | 2/2012 | Paquest et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bishay et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0108993 A1* | 5/2012 | Gordon ............... A61B 5/287 600/509 |
| 2012/0165645 A1 | 6/2012 | Russel et al. |
| 2012/0306662 A1 | 6/2012 | Vosch |
| 2012/0172695 A1 | 7/2012 | Ko et al. |
| 2012/0179665 A1 | 7/2012 | Baarman et al. |
| 2012/0184207 A1 | 7/2012 | Gaines |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0265080 A1 | 10/2012 | Yu et al. |
| 2012/0265738 A1 | 10/2012 | Beckmann et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0079618 A1 | 3/2013 | Sandmore et al. |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0124891 A1 | 5/2013 | Donaldson |
| 2013/0131530 A1 | 5/2013 | Brockway et al. |
| 2013/0158361 A1 | 6/2013 | Bardy |
| 2013/0172763 A1 | 7/2013 | Wheeler |
| 2013/0197380 A1 | 8/2013 | Oral et al. |
| 2013/0225963 A1 | 8/2013 | Kodandaramaiah et al. |
| 2013/0225966 A1 | 8/2013 | Barber et al. |
| 2013/0231947 A1 | 9/2013 | Shusterman |
| 2013/0243105 A1 | 9/2013 | Lei et al. |
| 2013/0274565 A1 | 10/2013 | Langer et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Barber et al. |
| 2014/0002234 A1 | 1/2014 | Alwan |
| 2014/0005502 A1 | 1/2014 | Klap et al. |
| 2014/0012154 A1 | 1/2014 | Mazar et al. |
| 2014/0031663 A1 | 1/2014 | Gallego |
| 2014/0056452 A1 | 2/2014 | Moss et al. |
| 2014/0088399 A1 | 3/2014 | Lian et al. |
| 2014/0107509 A1 | 4/2014 | Banet et al. |
| 2014/0121557 A1 | 5/2014 | Gannon et al. |
| 2014/0140359 A1 | 5/2014 | Kalevo et al. |
| 2014/0148718 A1 | 5/2014 | Stickney et al. |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0213937 A1 | 7/2014 | Bianchi et al. |
| 2014/0214134 A1 | 7/2014 | Peterson |
| 2014/0215246 A1 | 7/2014 | Lee et al. |
| 2014/0249852 A1 | 9/2014 | Proud |
| 2014/0296651 A1 | 10/2014 | Stone |
| 2014/0297310 A1 | 10/2014 | Collins |
| 2014/0318699 A1 | 10/2014 | Longinotti-Buitoni et al. |
| 2014/0324067 A1 | 10/2014 | Emken et al. |
| 2014/0330147 A1 | 11/2014 | Ousdigian et al. |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0018660 A1 | 1/2015 | Thomson et al. |
| 2015/0048836 A1 | 2/2015 | Guthrie et al. |
| 2015/0051472 A1 | 2/2015 | Wang et al. |
| 2015/0065842 A1 | 3/2015 | Lee et al. |
| 2015/0094558 A1 | 4/2015 | Russell |
| 2015/0142090 A1 | 5/2015 | Duijsens et al. |
| 2015/0164349 A1 | 6/2015 | Gopalakrishnan et al. |
| 2015/0165211 A1 | 6/2015 | Naqvi et al. |
| 2015/0177175 A1 | 6/2015 | Elder et al. |
| 2015/0202351 A1 | 7/2015 | Kaplan et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0324690 A1 | 11/2015 | Chilimbi et al. |
| 2015/0335285 A1 | 11/2015 | Poon et al. |
| 2015/0359489 A1 | 12/2015 | Baudenbacher et al. |
| 2016/0066850 A1 | 3/2016 | Brockway et al. |
| 2016/0135746 A1 | 5/2016 | Kumar et al. |
| 2016/0144190 A1 | 5/2016 | Cao et al. |
| 2016/0144192 A1 | 5/2016 | Sanghera et al. |
| 2016/0150982 A1 | 6/2016 | Roy |
| 2016/0196479 A1 | 7/2016 | Chertok et al. |
| 2016/0217369 A1 | 7/2016 | Annapureddy et al. |

(56) References Cited

U.S. PATENT DOCUMENTS

| | | | |
|---|---|---|---|
| 2016/0217691 A1 | 7/2016 | Kadobayashi et al. | |
| 2016/0235318 A1 | 8/2016 | Sarkar | |
| 2016/0235346 A1 | 8/2016 | Liu et al. | |
| 2017/0056650 A1 | 3/2017 | Cohen et al. | |
| 2017/0065207 A1* | 3/2017 | Landherr | A61N 1/37229 |
| 2017/0112399 A1 | 4/2017 | Brisben et al. | |
| 2017/0112401 A1 | 4/2017 | Rapin et al. | |
| 2017/0127964 A1 | 5/2017 | Moorman | |
| 2017/0156592 A1 | 6/2017 | Fu | |
| 2017/0032221 A1 | 7/2017 | Wu et al. | |
| 2017/0281032 A1 | 10/2017 | Weinberg et al. | |
| 2017/0281033 A1 | 10/2017 | Higgins et al. | |
| 2017/0340215 A1* | 11/2017 | Felix | A61B 5/335 |
| 2017/0354365 A1 | 12/2017 | Zhou | |
| 2017/0366921 A1 | 12/2017 | Pflugh et al. | |
| 2018/0020931 A1 | 1/2018 | Shusterman | |
| 2018/0042552 A1 | 2/2018 | Li et al. | |
| 2018/0078771 A1* | 3/2018 | Koop | A61B 5/349 |
| 2018/0116537 A1 | 5/2018 | Sullivan et al. | |
| 2018/0129893 A1 | 5/2018 | Son et al. | |
| 2018/0192965 A1 | 7/2018 | Rose et al. | |
| 2018/0256108 A1 | 9/2018 | Au-Yeung et al. | |
| 2018/0264258 A1 | 9/2018 | Cheng et al. | |
| 2018/0333058 A1 | 11/2018 | Coulon et al. | |
| 2019/0021671 A1 | 1/2019 | Kumar et al. | |
| 2019/0046038 A1 | 2/2019 | Weinstein et al. | |
| 2019/0059763 A1 | 2/2019 | Shakur et al. | |
| 2019/0069815 A1 | 3/2019 | Burnes et al. | |
| 2019/0117068 A1 | 4/2019 | Thomson et al. | |
| 2019/0336032 A1 | 11/2019 | Gill et al. | |
| 2020/0038671 A1 | 2/2020 | Schulhauser et al. | |
| 2020/0352441 A1 | 11/2020 | Soykan et al. | |

OTHER PUBLICATIONS

May 24, 2022 Letter to Opposing Counsel. 1:22-cv-00351-CFC. May 24, 2022.

Complaint from Case No. 1:22-cv-00351-UNA, *Bardy Diagnostics, Inc.* (Plaintiff) v. *Vital Connect, Inc.* (Defendant), Filed: Mar. 18, 2022, 182 pages.

Defendant's Opening Brief In Support of Its Motion To Dismiss For Failure to State A Claim from Case No. 1:22-ov-00351-CFC, *Bardy Diagnostics, Inc.* (Plaintiff) v. *Vital Connect, Inc.* (Defendant), Filed: May 25, 2022, 18 pages.

Defendant's Answer, Defenses, and Counterclaim from Case No. 1:22-cv-00351-CFC, *Bardy Diagnostics, Inc.* (Plaintiff) v. *Vital Connect, Inc.* (Defendant), Filed: May 25, 2022, 132 pages.

Plaintiff's Answering Brief In Opposition to Defendant's Motion to Dismiss For Failure to State a Claim from Case No. 1:22-cv-00351-CFC, *Bardy Diagnostics, Inc.* (Plaintiff) v. *Vital Connect, Inc.* (Defendant), Filed: Jun. 8, 2022, 25 pages.

Plaintiff's Answer to Defendant's Counterclaim from Case No. 1:22-cv-00351-CFC, *Bardy Diagnostics, Inc.* (Plaintiff) v. *Vital Connect, Inc.* (Defendant), Filed: Jun. 15, 2022, 5 pages.

Defendant's Reply Brief In Support of Its Motion to Dismiss For Failure to State a Claim from Case No. 1:22-cv-00351-CFC, *Bardy Diagnostics, Inc.* (Plaintiff) v. *Vital Connect, Inc.* (Defendant), Filed: Jun. 15, 2022, 93 pages.

Oct. 17, 2022 Letter to Opposing Counsel, *Bardy Diagnostics, Inc.* v. *Vital Connect, Inc.*, No. 22-cv-00351-CFC (D. Del.), Oct. 17, 2022.

Nov. 11, 2022, Letter from Opposing Counsel, 1:22-cv-00351-CJB; *Bardy Diagnostics, Inc.* v. *Vital Connect, Inc. (D. Del.)*, Nov. 11, 2022.

Dec. 26, 2022 Letter from Opposing Counsel, 1:22-cv-00351-CJB; *Bardy Diagnostics, Inc.* v. *Vital Connect, Inc. (D. Del.)*; and IPR2023-00381; *Vital Connect, Inc.* v. *Bardy Diagnostics, Inc. (P.T.A.B.)*, Dec. 26, 2022.

First Amended Complaint for Patent Infringement, 1:22-cv-00351-CJB, *Bardy Diagnostics, Inc.* v. *Vital Connect, Inc. (D. Del.)*, filed Jan. 10, 2023.

Petition for Inter Partes Review of U.S. Pat. No. 11,051,743 Pursuant To 35 U.S.C. §§ 311-319 and 37 C.F.R. §42, Case No. IPR2023-00381, *Vital Connect, Inc.* v. *Bardy Diagnostics, Inc. (P.T.A.B.)*, Dec. 21, 2022, 875 pages.

Defendant's Answer to First Amended Complaint, Defenses, and Counterclaim, 1:22-cv-00351-CJB, *Bardy Diagnostics, Inc.* v. *Vital Connect, Inc. (D. Del.)*, filed Jan. 24, 2023 (227 pages).

May 2, 2022 Letter From Counsel. 1:22-cv-00351-CFC. May 2, 2022.

\* cited by examiner

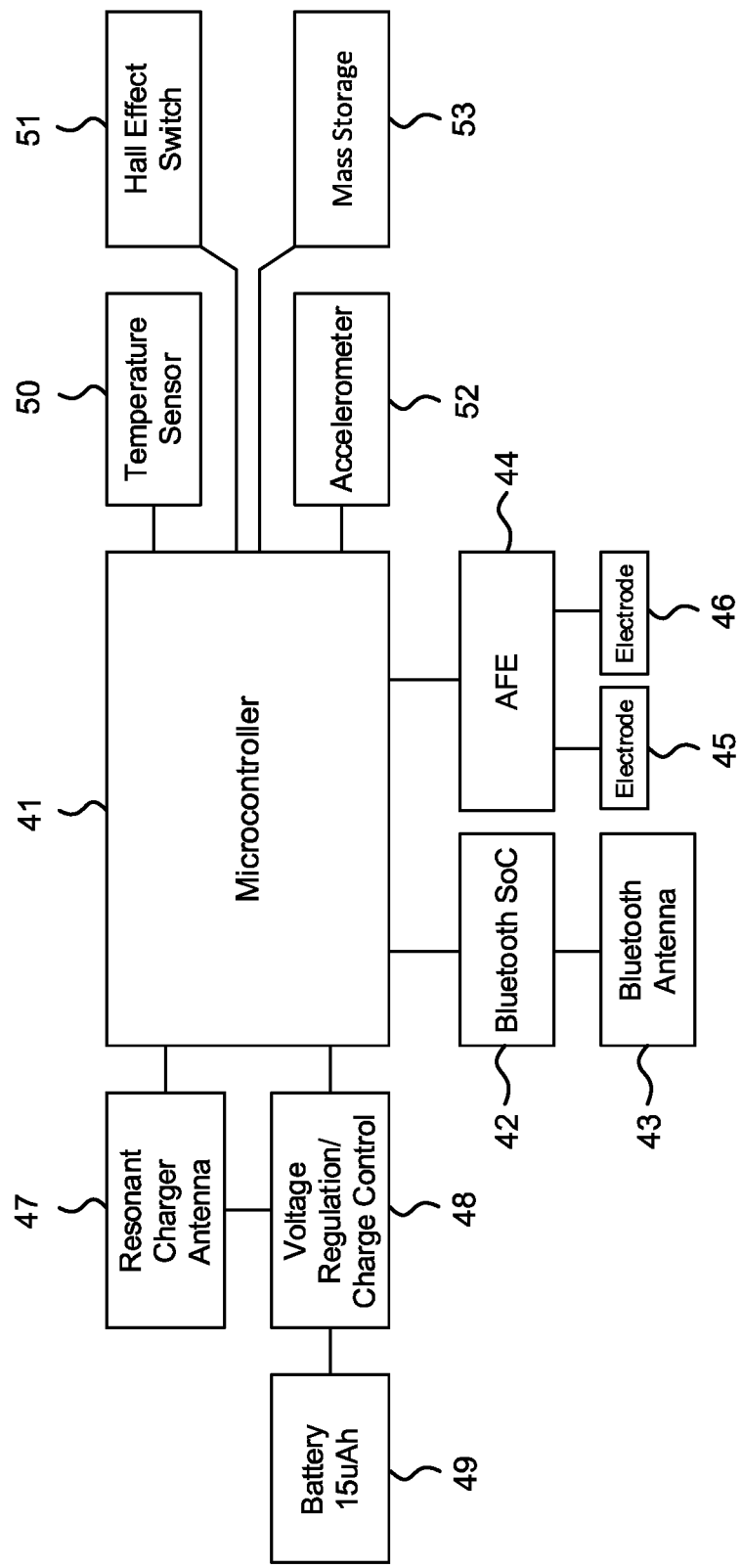

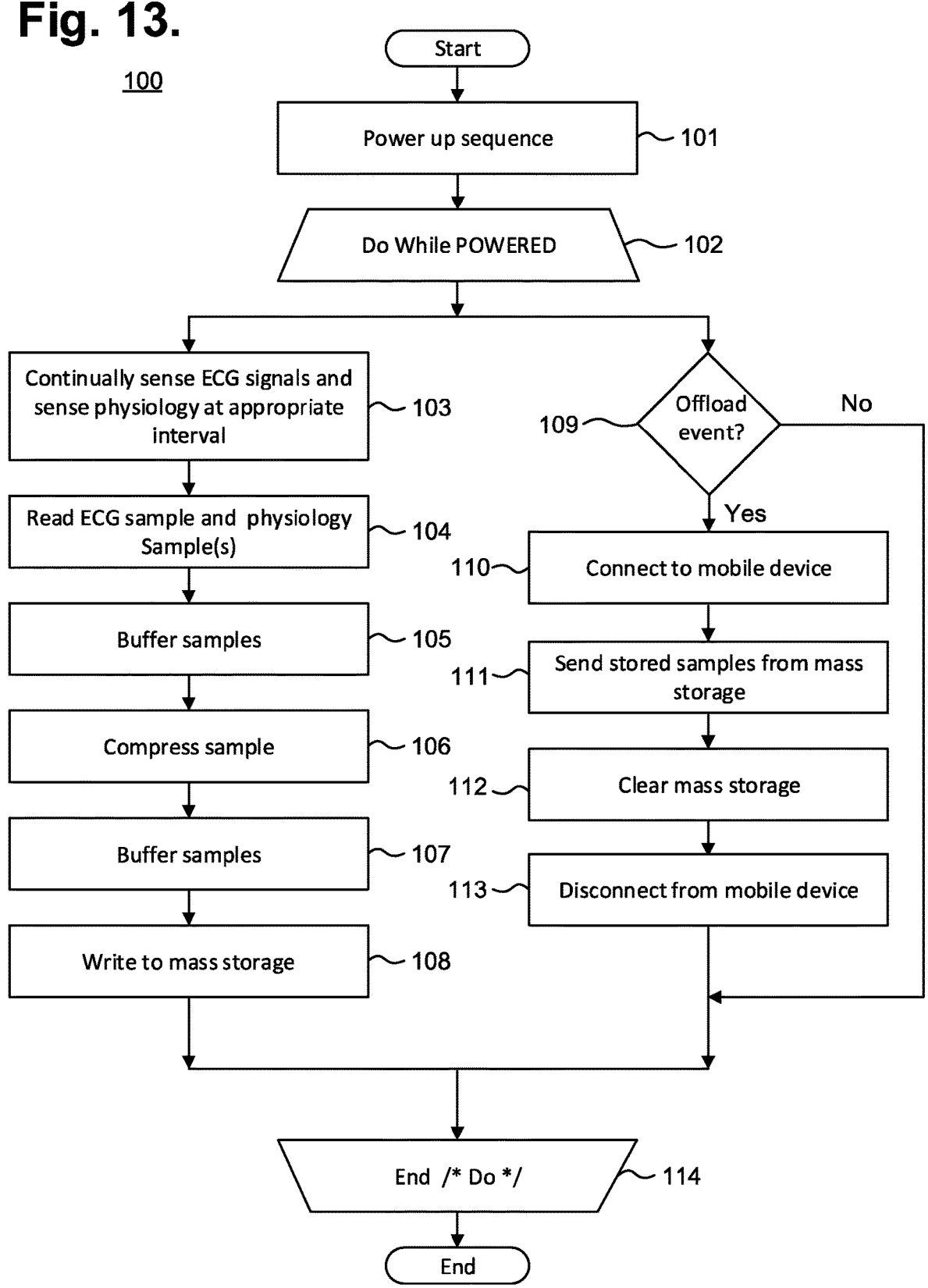

CONFIGURABLE HARDWARE PLATFORM FOR PHYSIOLOGICAL MONITORING OF A LIVING BODY

CROSS-REFERENCE TO RELATED APPLICATION

This non-provisional patent application claims priority under 35 U.S.C. § 119(e) to U.S. Provisional Patent application, Ser. No. 62/874,086, filed Jul. 15, 2019 and U.S. Provisional Patent application, Ser. No. 62/962,773, filed Jan. 17, 2020, pending, the disclosures of which are incorporated by reference. This non-provisional patent application is also a continuation-in-part of U.S. patent application Ser. No. 16/926,381, filed Jul. 10, 2020 pending, which claims priority under 35 U.S.C. § 119(e) to U.S. Provisional Patent application, Ser. No. 62/873,754, filed Jul. 12, 2019, U.S. Provisional Patent application, Ser. No. 62/874,086, filed Jul. 15, 2019, U.S. Provisional Patent application, Ser. No. 62/873,740, filed Jul. 12, 10 2019, U.S. Provisional Patent application, Ser. No. 62/962,773, filed Jan. 17, 2020, and is further a continuation-in-part of U.S. patent application Ser. No. 16/919,626, filed on Jul. 2, 2020, pending, which claims priority under 35 U.S.C. § 119(e) to U.S. Provisional Patent application, Ser. No. 62/870,506, filed Jul. 3, 2019, the disclosures of which are incorporated by reference.

FIELD

This application relates, in general, to health and medical apparatuses for sensing and recording the physiology of a living body and, in particular, to a configurable hardware platform for physiological monitoring of a living body.

BACKGROUND

Patient physiology is one of the four cornerstones of modern diagnostic medicine, which defines the structured process routinely employed by physicians and other medical professionals (henceforth, simply "physicians") to determine the nature and cause of patient health concerns and problems, and physicians need data on patient physiology that is timely, accurate, and reliable to provide effective health care. Through the diagnostic medicine process, a physician will make findings of possible diagnoses that can explain or match a patient's signs and symptoms in terms of a disease or medical condition, which thereby enables the physician to formulate a plan of treatment and follow-up care.

Medical diagnosis includes evaluating patient physiology, which describes the vital functions of the patient's anatomical structure, that is, the living body and its organs. A patient's physiology is determined through medical diagnostic procedures that include performing medical tests and, when available, reviewing patient data that has been collected through monitoring, although the data should first be correlated to patient symptoms to be of relevant diagnostic value.

Sporadic conditions present a special challenge because diagnostic tests performed in a physician's office may prove ineffective if the sporadic condition fails to present while the test is being performed. Sporadic conditions may be due to chronic or acute cause and can include transient signs, such as erratic heartbeat, muscle or nerve spasms, or hypoglycemia (or hyperglycemia) that may be accompanied by discernable symptoms. The unpredictable nature of sporadic conditions often makes the capturing of physiological data a matter of good timing. If the sporadic condition fails to occur during the course of a medical test, no physiological data, and therefore no diagnostic insight, is obtained.

In response, physicians have turned to ambulatory monitoring, which utilizes sensors placed cutaneously on or implanted within a patient's body that are attached to a recorder to provide physiological data capture while the patient goes about daily life. Ambulatory monitors include Holter monitors for electrocardiographic (ECG) monitoring, ambulatory blood pressure monitors (ABPM) for collecting blood pressure data at periodic intervals, and continuous glucose monitors that collect blood glucose data. Through ambulatory monitoring, physiological data may be captured and recorded continuously, upon demand for subsequent retrieval and evaluation, or might be recorded and reported in real or near real time, provided that the recorder is equipped with remote data communications capabilities using, for instance, cellular communications.

Ambulatory monitors that are either wholly implanted inside the patient's body or which use implanted sensors will generally provide cleaner physiological data relatively free of environmental noise and effects, especially when compared to data captured cutaneously. However, implantation is, by definition, invasive to some degree and carries more risk than cutaneous or external forms of ambulatory monitoring. Moreover, at least in part in light of the significance, complications, and expense of implantation, implanted forms of ambulatory monitors are also expected to be capable of operating over an extended period of time, so battery depletion must be considered to ensure sufficient service life. Thus, continuous recording of every heartbeat is not possible in conventional implantable ambulatory monitors due to power consumption and hard limits of onboard processing and storage, as continuous per-heartbeat monitoring places significant demands on these resources, which are strictly limited in an implantable device.

Typically, implanted forms of ambulatory monitors provide a single form of sensing into a patient's body using purpose-built hardware that will serve over the lifetime of the device, such as electrocardiographic electrodes. The associated recorder is similarly deployed to capture physiology through the sensing hardware by operating under a programming set that must accommodate an entire potential patient population. In some cases, additional programming complexity may be required to cover a minority of patients that nevertheless must be included in the programming set, albeit at the expense of conceivably dominating an engineering solution by requiring additional storage and computational resources.

Moreover, in conflict with the decision to provide a single form of sensing, an ambulatory monitoring environment is not static. A patient's body could (and likely will) change over time during the course of treatment, necessitating a different monitoring strategy or type of sensor for other forms of physiology. Notwithstanding, physicians are effectively limited to the hardware on-hand at the time of implanting. Such design tradeoffs, such as having only a single form of sensing and reliance upon a general purpose programming set, limit the abilities of implanted forms of conventional ambulatory monitors. New sensory capabilities cannot be added without implanting new sensing hardware, plus each new sensor must somehow be interfaced to the recorder, which will need to be able to handle the new sensor in terms of data capture, processing, and storage. Additional sensory capabilities may also adversely effect battery life, which can be of particular concern if the recorder lacks recharging capabilities and the intended service life of the implantable device could be negatively impacted.

Therefore, a need remains for an implanted form of ambulatory physiological monitor that offers per-heartbeat monitoring with flexible and extensible monitoring capabilities in terms of sensory capabilities, scope of device programming, and service life, without having to implant additional hardware.

SUMMARY

A configurable hardware platform for health and medical monitoring of physiology is housed within a hermetically sealed implantable medical device (IMD). Physically, the IMD has a generally tubular shape that includes a central tubular body with rounded semi spherical end caps. When configured to measure electrocardiographic signals, the central tubular body and one of the semi spherical end caps function as electrode dipoles. The semi spherical end cap is electrically conductive yet electrically insulated from the central tubular body. As well, the outside surface of the central tubular body is partially electrically insulated, generally on the surface closest to the electrically conductive semi spherical end cap to form a non-electrically conductive inversion with only the outside surface distal to that semi spherical end cap being exposed.

When placed within the central tubular body, a flexible circuit board forms three aspects of a microcontroller circuit assembly that respectively define a receiving coil for inductive charging and optional communication, a high frequency antenna for radio frequency (RF) data exchange, and a flexible circuit board containing a microcontroller and device circuitry. An onboard power source that includes a rechargeable energy cell, battery, or supercapacitor is also placed within the tubular body to one end of the flexible circuit board and, optionally, in electrical contact through a protection circuit with the electrically conductive semi spherical end cap, thereby serving as an electrical feedthrough to the flexible circuit board. The power source may be recharged through a charging and conditioning circuit interfaced with the microcontroller using a non-contact method, such as inductive charging, resonant charging, energy harvesting, thermal gradient charging, ultrasonic charging, RF-based charging or charging by ambient or driven motion.

The IMD can provide continuous monitoring of the patient on a heartbeat-by-heartbeat basis. The monitoring data is regularly offloaded through live transmission or delayed transmission, which may occur, for instance, two days or longer following recordation, or live monitoring. The offloaded monitoring data is analyzed at a datacenter, where the processing constraints imposed by the computational and resource limits of the IMD are not a hindrance. Additionally, the IMD is equipped with one or more physiological or non-physiological sensors that can be selectively activated over the implantation lifetime to tailor the monitoring of the patient to ongoing diagnostic needs. The physiological sensors non-exhaustively include ECG, temperature, oxygen saturation, respiration, blood glucose, and sensors which detect movement, position, or acceleration.

One embodiment provides an implantable medical device. A housing includes a hollow body forming a first electrode on an outer surface with end caps affixed to opposite ends, one such end cap forming a second electrode on an outer surface. A microcontroller circuit is provided circumferentially within the housing and includes a microcontroller operable under program instructions stored within a non-volatile memory device. An analog front end is electrically interfaced to the first and the second electrodes and is operable to sense electrocardiographic signals. A transceiver circuit is operable to wirelessly communicate with an external data device. The program instructions define instructions for the microcontroller to continuously sample the electrocardiographic signals into the non-volatile memory device and to offload the non-volatile memory device to the external data device via the transceiver circuit. A receiving coil and a charging circuit are operable to charge an onboard power source for the microcontroller circuit.

Another embodiment provides an implantable medical device. A cylindrical hollow body forms a first electrode on an outer surface. A first spherical end cap is attached on one end of the hollow body. A second spherical end cap is attached on an other end of the hollow body and forms a second electrode on an outer surface. Electronic circuitry is housed within the hollow body. A microcontroller is operable under program instructions contained in microcode stored within a non-volatile memory device. A physiological sensor is operable to sense physiological data and is electrically interfaced to the microcontroller. An analog front end is electrically interfaced to the first and the second electrodes and the microcontroller and operable to sense electrocardiographic signals. A transceiver circuit is electrically interfaced to a high frequency antenna housed within the second spherical end cap and the microcontroller and is operable to wirelessly communicate with an external data device. A receiving coil is formed as part of a non-contact charging circuit. The program instructions are operable to instruct the microcontroller to continuously sample the electrocardiographic signals and the physiological data at set times into the non-volatile memory device and to offload the non-volatile memory device to the external data device via the transceiver circuit. A power source is housed within the hollow body and is electrically interfaced to the non-contact charging circuit. The power source is operable to power the microcontroller.

Yet another embodiment provides an implantable medical device. A main cylindrical body defines an axial bore extending longitudinally over the length of the main cylindrical body and exposes an electrically conductive area defining a first electrode on at least part of the outer surface of the main cylindrical body. A protective spherical end cap is fixedly disposed on one end of the main cylindrical body and defines an interior cavity. The protective spherical end cap further exposes an electrically conductive area defining a second electrode on at least part of the outer surface of the protective spherical end cap. An antenna spherical end cap is fixedly disposed on one end of the main cylindrical body and defines an interior cavity with a high frequency antenna housed within. A printed circuit board is housed within the main cylindrical body. Electronic circuitry includes a physiological sensor operable to sense physiological data. The electronic circuitry also includes an analog front end electrically interfaced to the first and the second electrodes and operable to sense electrocardiographic signals. A transceiver circuit is electrically interfaced to the high frequency antenna and is operable to wirelessly communicate with an external data device. A microcontroller is operable under program instructions contained in microcode stored within a non-volatile memory device and is electrically interfaced with a physiological sensor, the analog front end, and the transceiver circuit. The microcontroller is operable under the program instructions to record the physiological data at set times and the electrocardiographic signals continuously into the non-volatile memory device and to offload the electrocardiographic signals from the non-volatile memory device to the external data device. A receiving coil is formed on an extended surface of the printed circuit board that is adapted to be circumferentially disposed about the electronic circuitry and is provided as part of a non-contact charging circuit. A power source comprising a rechargeable energy cell housed within the main cylindrical body and electrically interfaced with the charging circuit to power the electronic circuitry.

The configurable hardware platform provides several advantages over conventional designs, including rapid recharging, a flexible and extensible hardware platform, the ability to provide full and complete disclosure of physiological recording data (in contrast to binned, averaged, event-based or other forms of telemetric disclosure), continuous monitoring, store and forward functionality, and the ability to serve as an extended or lifetime monitor.

Still other embodiments will become readily apparent to those skilled in the art from the following detailed description, wherein are described embodiments by way of illustrating the best mode contemplated. As will be realized, other and different embodiments are possible, and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

FIG. 12 is a block diagram showing the microarchitecture of the IMD of FIG. 1.

FIG. 13 is a flow diagram showing a method for continuously monitoring electrocardiography for use in the IMD of FIG. 1.

DETAILED DESCRIPTION

Related Applications

Figure 1:
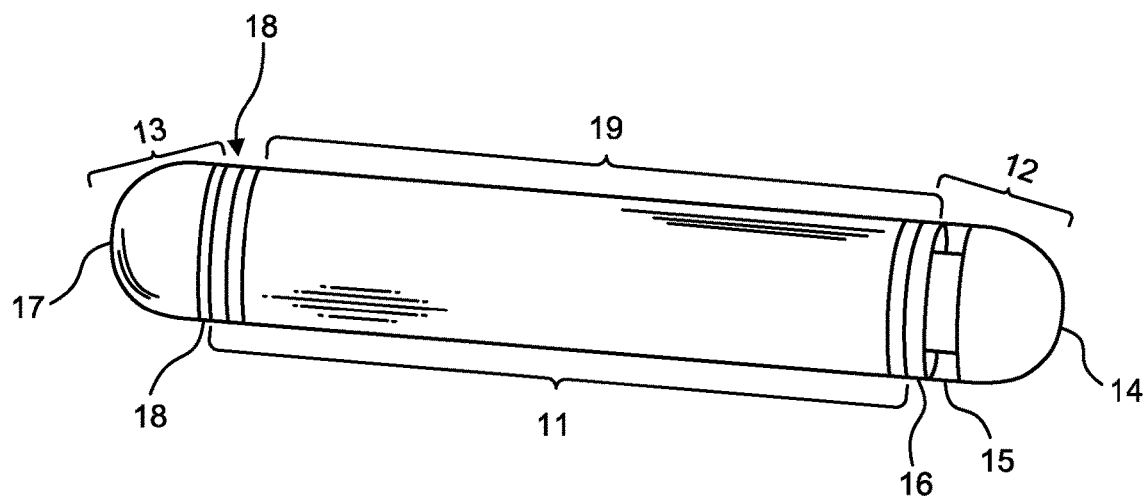
FIG. 1 is an outer perspective view showing an IMD that houses a configurable hardware platform for physiological monitoring of a living body in accordance with one embodiment.

This non-provisional patent application is related to in commonly-assigned U.S. Pat. No. 9,545,204, issued Jan. 17, 2017 to Bishay et al.; U.S. Pat. No. 9,730,593, issued Aug. 15, 2017 to Felix et al.; U.S. Pat. No. 9,717,432, issued Aug. 1, 2017 to Felix et al.; U.S. Pat. No. 9,775,536, issued Oct. 3, 2017 to Felix et al.; U.S. Pat. No. 9,433,380, issued Sep. 6, 2016 to Bishay et al.; U.S. Pat. No. 9,655,538, issued May 23, 2017 to Felix et al.; U.S. Pat. No. 9,364,155, issued Jun. 14, 2016 to Bardy et al.; U.S. Pat. No. 9,737,224, issued Aug. 22, 2017 to Bardy et al.; U.S. Pat. No. 9,433,367, issued Sep. 6, 2016 to Felix et al.; U.S. Pat. No. 9,700,227, issued Jul. 11, 2017 to Bishay et al.; U.S. Pat. No. 9,717,433, issued Aug. 1, 2017 to Felix et al.; U.S. Pat. No. 9,615,763, issued Apr. 11, 2017 to Felix et al.; U.S. Pat. No. 9,642,537, issued May 9, 2017 to Felix et al.; U.S. Pat. No. 9,408,545, issued Aug. 9, 2016 to Felix et al.; U.S. Pat. No. 9,655,537, issued May 23, 2017 to Bardy et al.; U.S. Pat. No. 10,165,946, issued Jan. 1, 2019 to Bardy et al.; U.S. Pat. No. 10,433,748, issued Oct. 8, 2019, to Bishay et al.; U.S. Pat. No. 10,667,711, issued Jun. 2, 2020, to Felix et al.; U.S. Pat. No. 9,619,660, issued Apr. 11, 2017 to Felix et al.; U.S. Pat. No. 10,463,269, issued Nov. 5, 2019 to Boleyn et al.; U.S. Pat. No. 9,408,551, issued Aug. 9, 2016 to Bardy et al.; U.S. Patent Application Publication No. 2019/0069800, published Mar. 7, 2019 to Bardy et al.; U.S. Patent Application Publication No. 2019/0069798, published Mar. 7, 2019 to Bardy et al.; U.S. Patent Application Publication No. 2019/0117099, published Apr. 25, 2019 to Bardy et al.; U.S. Patent Application Publication No. 2019/0099105, published Apr. 4, 2019 to Felix et al.; U.S. Pat. No. 10,624,551, issued Apr. 21, 2020 to Bardy et al.; U.S. Pat. No. 10,251,576, issued Apr. 9, 2019 to Bardy et al.; U.S. Pat. No. 9,345,414, issued May 24, 2016 to Bardy et al.; U.S. Pat. No. 10,433,751, issued Oct. 8, 2019 to Bardy et al.; U.S. Pat. No. 9,504,423, issued Nov. 29, 2016 to Bardy et al.; U.S. Patent Application Publication No. 2019/0167139, published Jun. 6, 2019 to Bardy et al.; U.S. Design Pat. No. D717955, issued Nov. 18, 2014 to Bishay et al.; U.S. Design Pat. No. D744659, issued Dec. 1, 2015 to Bishay et al.; U.S. Design Pat. No. D838370, issued Jan. 15, 2019 to Bardy et al.; U.S. Design Pat. No. D801528, issued Oct. 31, 2017 to Bardy et al.; U.S. Design Pat. No. D766447, issued Sep. 13, 2016 to Bishay et al.; U.S. Design Pat. No. D793566, issued Aug. 1, 2017 to Bishay et al.; U.S. Design Pat. No. D831833, issued Oct. 23, 2018 to Bishay et al.; and U.S. Design Pat. Application Ser. No. 29/612,334, entitled: "Extended Wear Electrode Patch," filed Jul. 31, 2017, pending; U.S. patent application Ser. No. 16/919,626, filed on Jul. 2, 2020, entitled "Subcutaneous P-Wave Centric Insertable Cardiac Monitor With Energy Harvesting Capabilities," pending; and U.S. patent application Ser. No. 16/926,381, filed Jul. 10, 2020, entitled "System and Method for Remote ECG Data Streaming in Real-Time," pending, the disclosures of which are incorporated by reference.

Overview

A configurable hardware platform for health and medical monitoring of physiology is housed within a hermetically sealed, implantable medical device (IMD). The IMD provides an implanted form of ambulatory physiological monitor that offers per-heartbeat monitoring with flexible and extensible monitoring capabilities. The IMD is designed to be implanted within a living body and to operate over an extended time period while monitoring different types of patient physiology, possibly at different times and in different ways.

The IMD can record every heartbeat, perform live transmission or delayed transmission, which may occur, for instance, two days or longer following recordation, or live monitoring. When every heartbeat is recorded and sent, the platform does not require an analysis algorithm onboard; rather, the analysis algorithm could be implemented at a datacenter or on a cell phone to do the heavy data processing by utilizing the better computing resources available on those platforms. The IMD is equipped with one or more physiological sensors that non-exhaustively include ECG, temperature, pulse oximetry, oxygen saturation, respiration, blood glucose, blood pressure, and drug levels or any appropriate measure of disease. In a further embodiment, the IMD can also monitor non-physiological data when the IMD is equipped with an appropriate type of sensor, such as posture as derived from data measured by an actigraphy sensor, accelerometer or inertial motion sensor. Other types of sensors and forms of physiology and non-physiological data capture are possible, such as cardiac effort level, thoracic impedance, and sound recording, including ultrasonic and sub-sonic sound recording.

The degree of surgical invasiveness required to implant the IMD depends upon the intended situs within the body, which is at least in part dictated by the desired range of physiology to be monitored. For instance, electrocardiographic monitoring of the heart that emphasizes the propagation of low amplitude, relatively low frequency content cardiac action potentials, particularly the P-waves that are generated during atrial activation, can be efficaciously performed by implanting the IMD in a subcutaneous situs located axially and slightly to either the left or right of the sternal midline in the parasternal region of the chest. This type of subcutaneous implantation can be performed in a physician's office using a specialized implantation instrument that includes a trocar to incise the skin and form a subcutaneous tunnel, and a cannula through which the IMD is guided into place, after which the implantation instrument is withdrawn and the surgical incision is closed.

Specific details of the IMD's housing, electronic and support circuitry, power source, and microarchitecture will now be discussed.

Housing

Physically, the IMD has a generally cylindrical shape that includes a central tubular body with rounded semi spherical end caps, although other shapes and configurations are possible. In a further embodiment, one or both of the semi spherical end caps may be replaced pointed or semi-pointed tips to ease insertion into the body. FIG. 1 is an outer perspective view showing an IMD 10 that houses a configurable hardware platform for physiological monitoring of a living body in accordance with one embodiment. The IMD 10 includes three primary assemblies. The main middle section of the IMD 10 is a central body 11 that can be formed from a medical grade titanium or similar medical implantation-safe material. The central body 11 has a tubular or cylindrical shape that defines an axial bore, which provides a hollow interior cavity that is open on both end caps running longitudinally over the length of the central body 11. Other shapes having non-circular or non-spherical shapes are possible. Rounded semi spherical end caps 12 and 13 are welded or affixed to the central body 11 to form a hermetically sealed device housing. The end caps 12 and 13 can be formed in other shapes, such as pointed or semi-pointed tips.

The central body 11 houses a flexible circuit board, a low frequency resonant charger antenna to facilitate device recharging, and an onboard power source generally consisting of a rechargeable energy cell, battery, or supercapacitor. One of the semi spherical end caps, known as the "Protectrode" 12, serves a dual purpose as an electrode and housing for patient and device protection components. The other semi spherical end cap, known as the "Radome" 13, houses a high frequency antenna used for transmitting data over an RF link, using, for instance, Bluetooth or WiFi. Additionally, the "Radome" 13 could be used to house an inductive antenna and inductive link. The RF link may also be used for device calibration and configuration. In a further embodiment, the "Radome" 13 can also house physiological sensors, such as pulse oximetry and blood pressure. In a further embodiment, the optically clear "Radome" 13 may allow light or other forms of radiation to be received and transmitted through to passively facilitate collection of other vital signs, such as pulse oximetry and blood pressure. In a still further embodiment, fiber optics or lenses implanted into the "Radome" 13 may facilitate collection of vital signs by sensors housed elsewhere.

The IMD 10 has an overall length of approximately 5.5 cm to 8.5 cm with an outer diameter, measured across the central body 11, of approximately 5-8 mm and a wall thickness of approximately 0.3 mm; however, other dimensions, including overall length, wall thickness, and outer diameter, are possible depending upon both the electronic circuitry and power source that need to be housed within and the types and numbers of physiological and non-physiological sensors.

In a further embodiment, the IMD 10 can be filled with a gas, such as argon or other inert gas. In particular, argon gas is conventionally used when welding titanium components and, when oxygen-purged into the interior of the IMD 10, further serves to preserve the electrical components and facilitate device longevity. In addition, supporting structure, such as an acrylic rod, can be used as an internal spacer to help keep the internal components in proper position.

In one embodiment, the central body 11 and the "Protectrode" 12 can be micro bead blasted to respectively increase the roughness of the central body 11 to improve silicone or Parylene bonding and to increase the surface area of the "Protectrode" 12 for better signal quality. A titanium nitride coating could also be applied to dramatically increase the surface area of the device.

The conductive surface 18 is formed by partially insulating the outside surface of the central body 11 using a non-electrically conductive, insulating surface treatment or coating ("insulating coating") 19. The insulating coating 19 is generally applied on the outer surface closest to the "Protectrode" 12, which maximizes the electrode dipole spacing. In one embodiment, the insulating coating 19 can be a chemical vapor deposited poly polymer, such as Parylene C. In a further embodiment, the insulating coating 19 can be a silicone polymer-based (polysiloxanes) coating. Alternatively, both forms of coatings, poly polymer and silicone polymer, could be employed. Poly polymers exhibit superior moisture resistance and insulation resistance properties, but are susceptible to damage from scratches and scrapes. Silicone polymer coatings form a durable protective layer and, when applied over a poly polymer coating, such as Parylene C, can protect the underlying coating from scratches and scrapes during insertion, repositioning, or removal of the IMD 10.

The end 22 of the central body 11 closest to the conductive surface 18 interfaces to the "Radome" 13. In one embodiment, the high frequency antenna is a separate component that is contained within the "Radome" 13. Here, the high frequency antenna can be held in place by filling the cavity of the "Radome" 13 with a filler material, such as acrylic, urethane, glass, or similar material, and the high frequency antennal is interfaced to a flexible circuit board via an electrical contact 20 that can be soldered or bonded to the high frequency antenna. In a further embodiment, the high frequency antenna is formed on a foldable "ear" section of the flexible circuit board and routed into the "Radome" 13 assembly.

Figure 2:
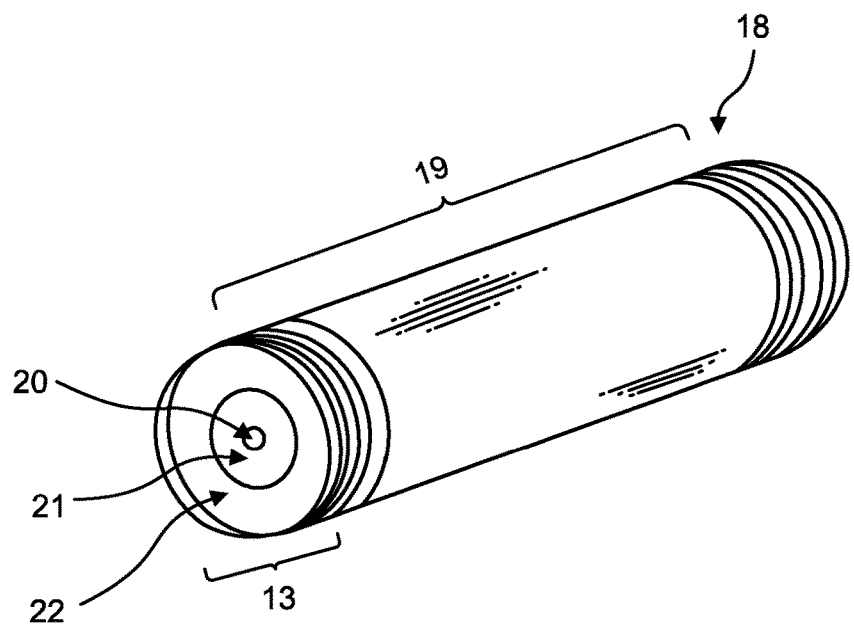
FIG. 2 is an outer perspective view showing the central tubular body of the IMD of FIG. 1.

In one embodiment, when configured to measure electrocardiographic signals, the "Protectrode" 12 and an exposed, conductive surface 18 of the central body 11 function as an electrode dipole. Other forms of electrode dipoles are possible. FIG. 2 is an outer perspective view showing the central body 11 of the IMD 10 of FIG. 1. The end cap 14 of the "Protectrode" 12 forms one electrode. An exposed, conductive surface 18 of the central body 11 distal to the "Protectrode" 12 forms the other electrode. The metallic case of the power source provides an electrical feedthrough from the "Protectrode" 12 to a flexible circuit board, thereby simplifying construction.

"Radome"

Figure 3:
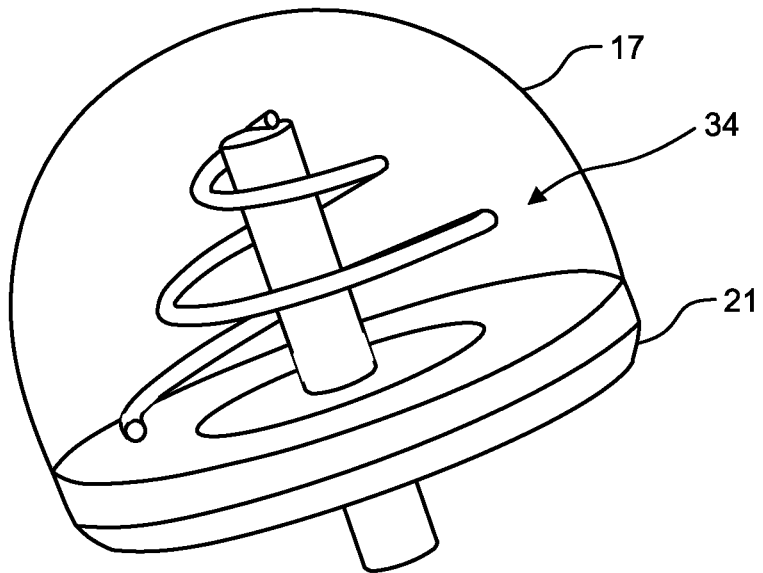
FIG. 3 is a side perspective view showing the semi spherical end cap ("Radome") of the IMD of FIG. 1.

Informally, the non-electrically conductive semi spherical end cap forms a "Radome" (radar dome) 13 that serves as a housing for a high frequency antenna used for RF data exchange. FIG. 3 is a side perspective view showing the semi spherical end cap ("Radome") of the IMD 10 of FIG. 1. A high frequency antenna 34 for data exchange is housed within the "Radome" 13. Note that more than one high frequency antenna could be included. The "Radome" 13 is an assembly that includes an electrically insulated semi sphere 17 formed from a medical implantation-safe grade material, such as acrylic, glass, ruby crystal, or ceramic, and a metallic weld ring 21 formed from a medical grade titanium or similar medical implantation-safe metal. These parts are bonded together using pressure fitting, brazing, laser welding, or electron beam welding. In a further embodiment, the high frequency antenna is defined as part of a flexible circuit board or folded metal shape, folded wire, or other similar structure, as further described infra.

"Protectrode"

Figure 4:
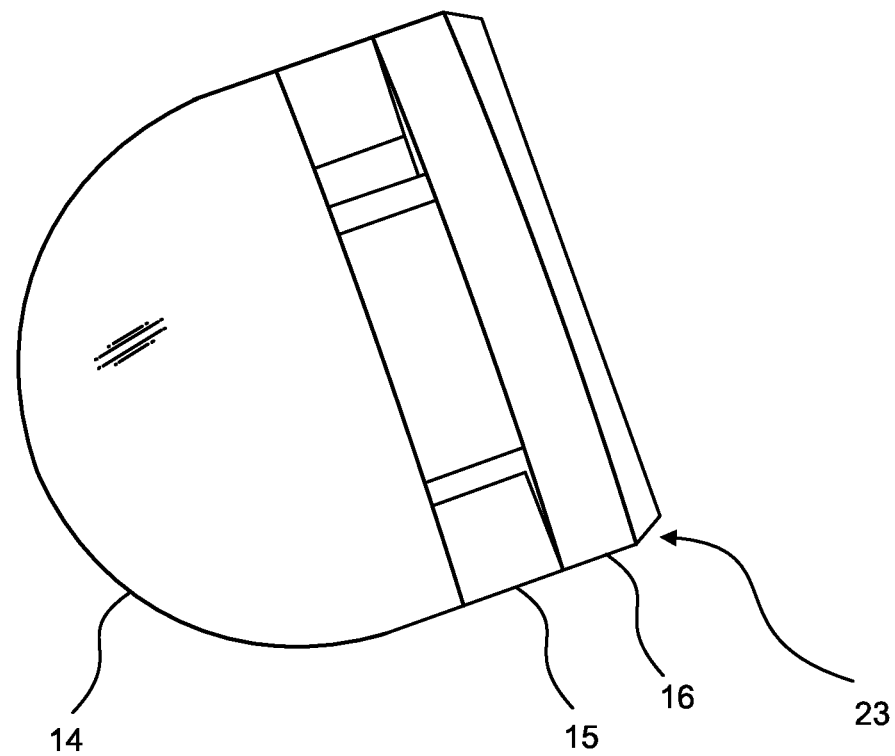
FIG. 4 is a side perspective view showing the electrically conductive semi spherical end cap ("Protectrode") of the IMD of FIG. 1.

Informally, the electrically conductive semi spherical end cap forms a "Protectrode" (feeder electrode) 12 that serves a dual purpose as an electrode and as housing for patient and device protection components. FIG. 4 is a side perspective view showing the electrically conductive semi spherical end cap ("Protectrode") of the IMD 10 of FIG. 1. The "Protectrode" 12 is an assembly that includes an electrically conductive semi sphere 14 formed from a medical grade titanium or similar medical implantation-safe conductor, an insulator ring 15 formed from a medical implantation-safe grade material, such as acrylic, glass, ruby crystal, or ceramic, and a metallic weld ring 16, which can include a chamfered edge 23 to facilitate welding to the central body 11, formed from a medical grade titanium or similar medical implantation-safe metal. These parts are bonded together with heat fitting, press fitting, brazing, epoxy adhesive, silicon adhesive or other similar bonding agent.

Figure 5:
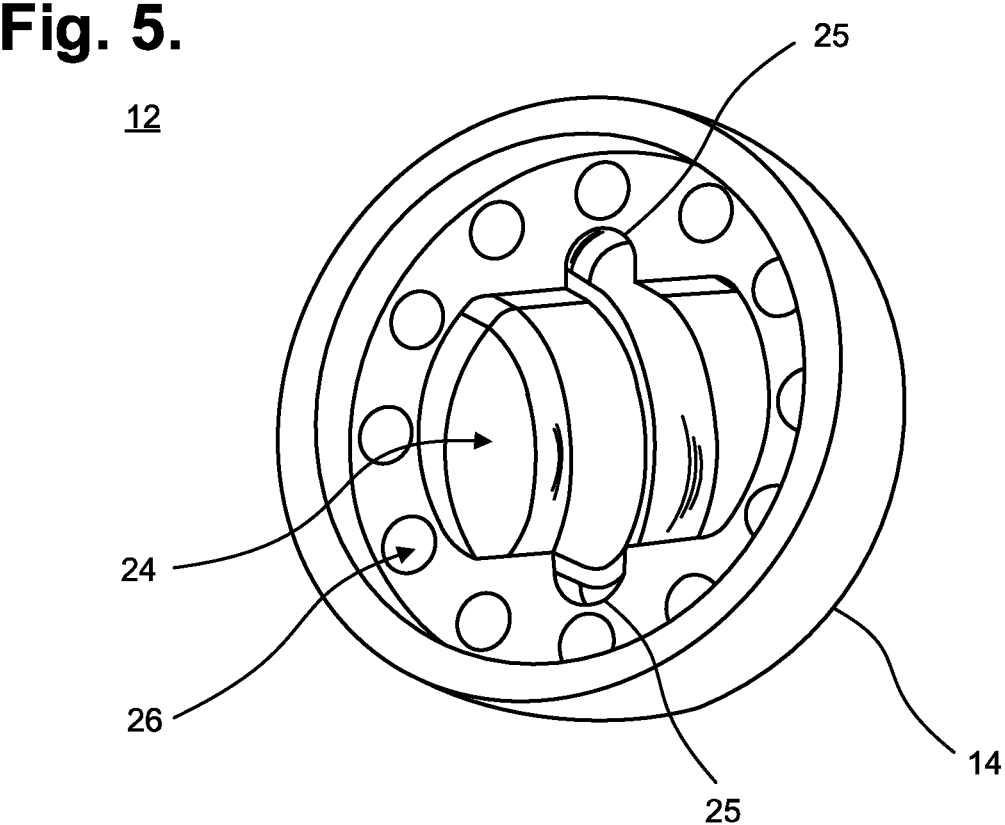
FIG. 5 is an inside perspective view showing the interior of the end cap of the "Protectrode" of FIG. 4.
Figure 6:
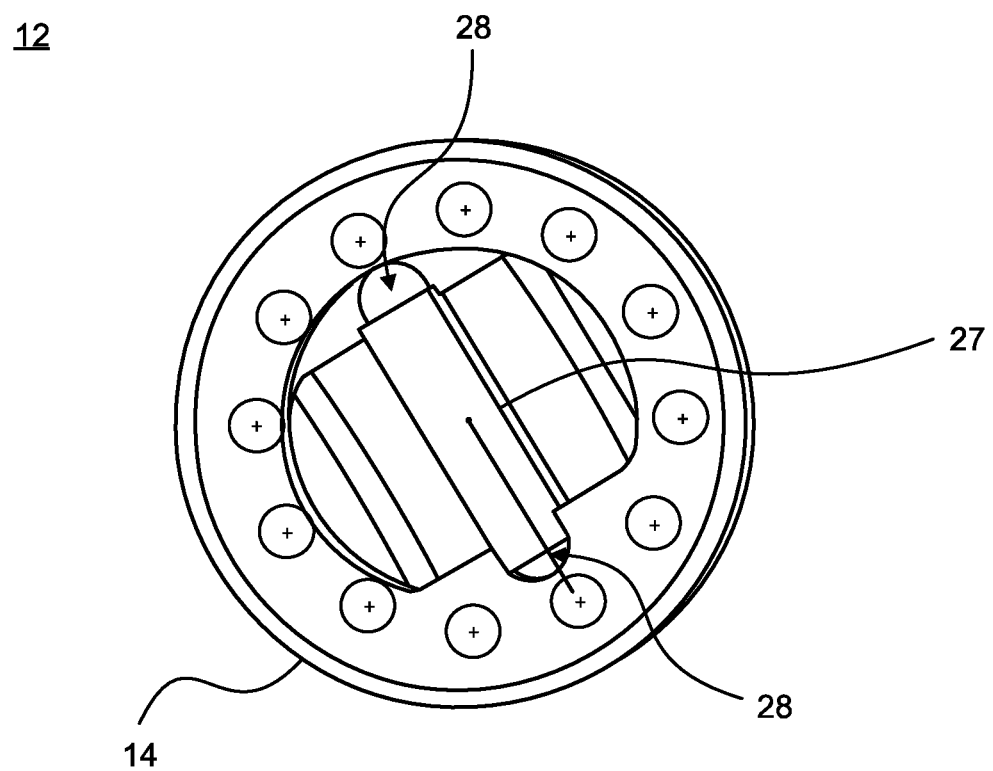
FIG. 6 is an inside perspective view showing the interior of the end cap of the "Protectrode" of FIG. 4.

The construction details of the "Protectrode" 12 will now be discussed. FIG. 5 is an inside perspective view showing the interior of the end cap 14 of the "Protectrode" 12 of FIG. 4. In one embodiment, a set of concave dimples 26 is formed along an inside shelf surface of the end cap 14. The dimples 26 increase surface area and thereby facilitate adhesion of the end cap 14 to the insulator ring 15, they also resist circular rotation. FIG. 6 is an inside perspective view showing the interior of the end cap 14 of the "Protectrode" 12 of FIG. 4. A circumferential groove 25 is longitudinally defined within a cavity 24 inside the end cap 14. The groove 25 provides a mounting location for a circuit board 27. The edges of the circuit board 27 are plated with a set of electrically conductive coatings 28 that include, starting from the circuit board 27 and proceeding outward, copper, nickel (thickly applied), palladium (thinly applied), and gold (of medium thickness), although other materials and combinations of layers are possible. The conductive coatings 28 are necessary to ensure against a galvanic reaction between the copper traces of the circuit board 27 and the titanium shell of the end cap 14. The "Protectrode" may be filled with epoxy or a similar material such as silicon to increase strength and dielectric breakdown properties and provide resistance to corrosion. The filler also will bond with the insulator when the insulator is made out of a brittle material such as ruby, glass or ceramic. The adhesive will hold in place the brittle material should the material fracture during an extreme impact event, such as a car crash.

Figure 7:
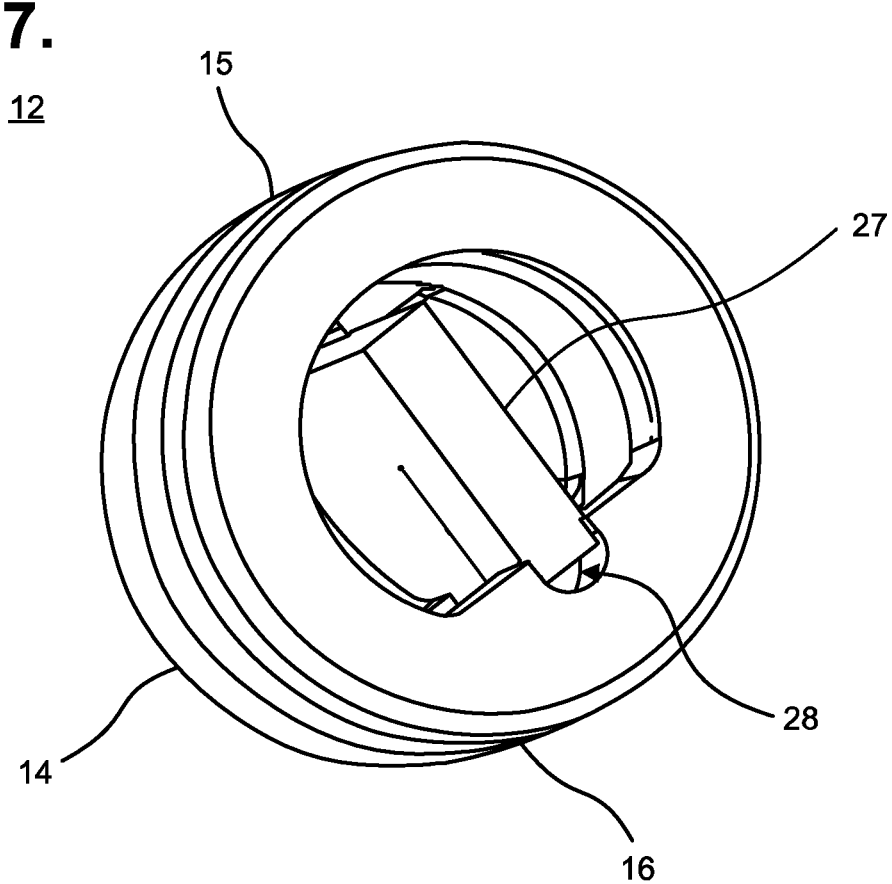
FIG. 7 is an inside perspective view showing the interior of the fully assembled "Protectrode" of FIG. 4.

FIG. 7 is an inside perspective view showing the interior of the fully assembled "Protectrode" 12 of FIG. 4. The edges of the circuit board 27 contact the "Protectrode" 12 along the groove 25. The edges of the circuit board 27 contact the "Protectrode" 12 in two places, in the groove 25 along the end cap 14 and in the groove 25 along the metallic weld ring 16 (the groove 25 is formed along only one side of the metallic weld ring 16, but could be formed along both sides).

Figure 8:
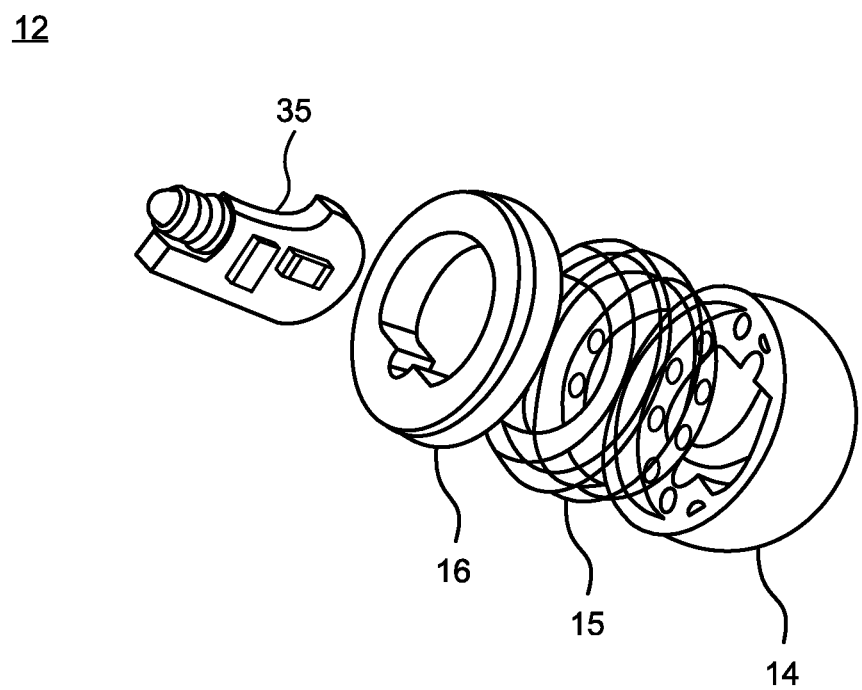
FIG. 8 is an exploded perspective view showing the components of the "Protectrode" of FIG. 4.

FIG. 8 is an exploded perspective view showing the components of the "Protectrode" of FIG. 4. The circuit board 27 includes a protection circuit 35 for the electrode dipole. The insulator ring 15 electrically isolates these two contact points, thereby allowing the protection circuit 35 to interface with both electrodes, that is, the "Protectrode" 12 and the conductive surface 18.

Flexible Circuit Board

The primary electrical structure of the IMD 10 is made out of a single flexible circuit board, which effectively eliminates many inter-circuit board connections and the delicate construction required to create them.

Folded Shape

Figure 9:
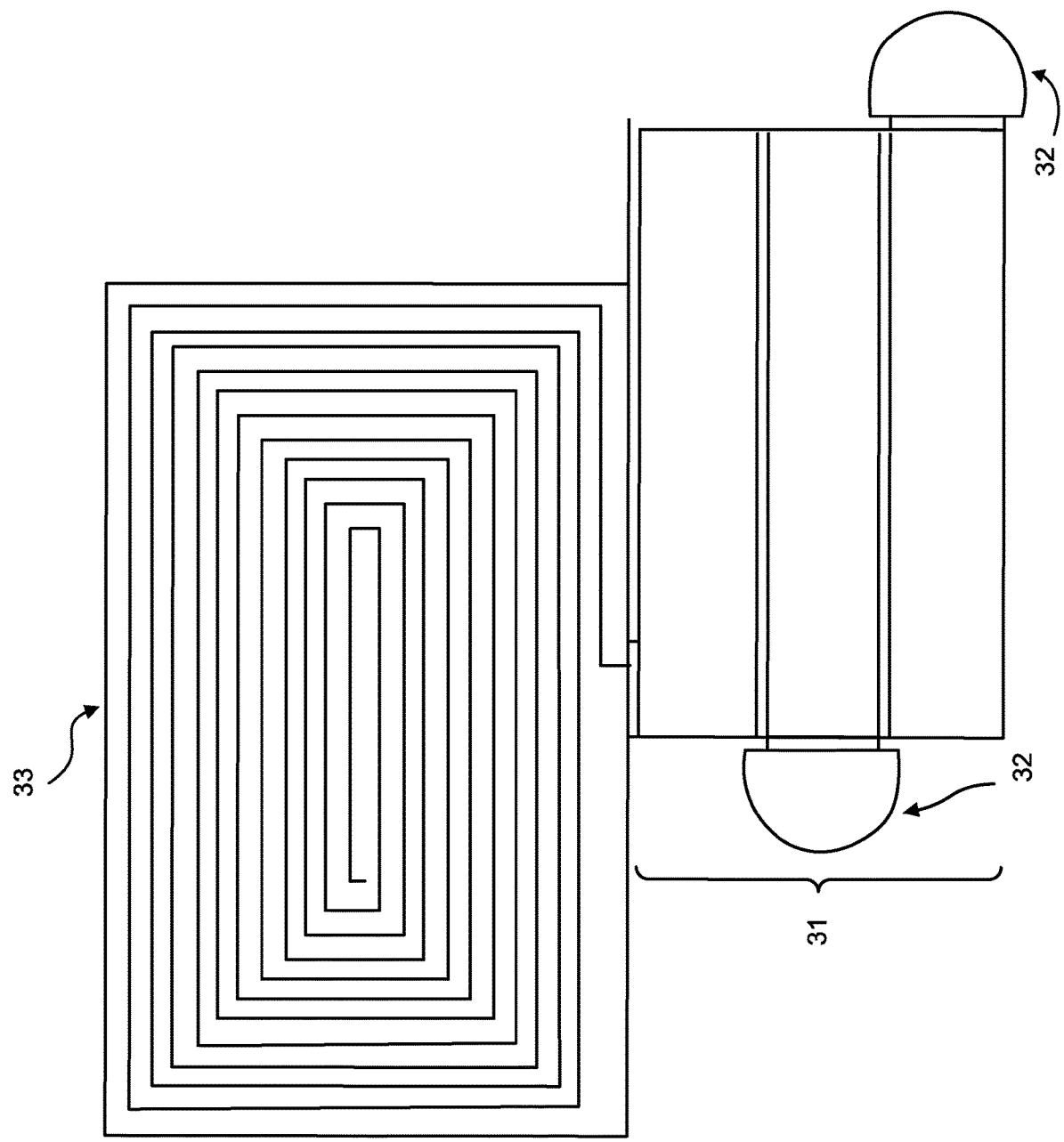
FIG. 9 is a top plan view of a flexible circuit board for use in the IMD of FIG. 1 in a flat, unfolded form.

The flexible circuit board 30 resembles a piece of origami paper that is folded into final shape, which is expected to increase device longevity and reliability by simplifying the design and eliminate the commonly-encountered failure points found in traditional designs. FIG. 9 is a top plan view of a flexible circuit board 30 for use in the IMD 10 of FIG. 1 in a flat, unfolded form. The flexible circuit board 30 is formed out of a single piece of flexible circuit board substrate defining a flexible circuit board 30 for placement of the microcontroller and device circuitry, a pair of vertically disposed foldable "ears" 32 provided on opposite ends of the flexible circuit board 30, and a foldable (or rollable) area 33 that acts as a receiving coil for inductive power coupling. On one end of the flexible circuit board 30, a foldable ear 32 connects to a power source and the feedthrough provided by the power source's case. On the other end of the flexible circuit board 30, the foldable ear 32 either connects to a high frequency antenna that is a separate component contained within the "Radome" 13 or the foldable ear 32 itself forms the high frequency antenna 23. The flexible circuit board 30 can include circuit traces on all sides, or multiple layers covered by an insulating layers to maximize space utilization. In one embodiment, the receiving coil's circuit traces are copper, although other types of conductive materials could be used.

Figure 10:
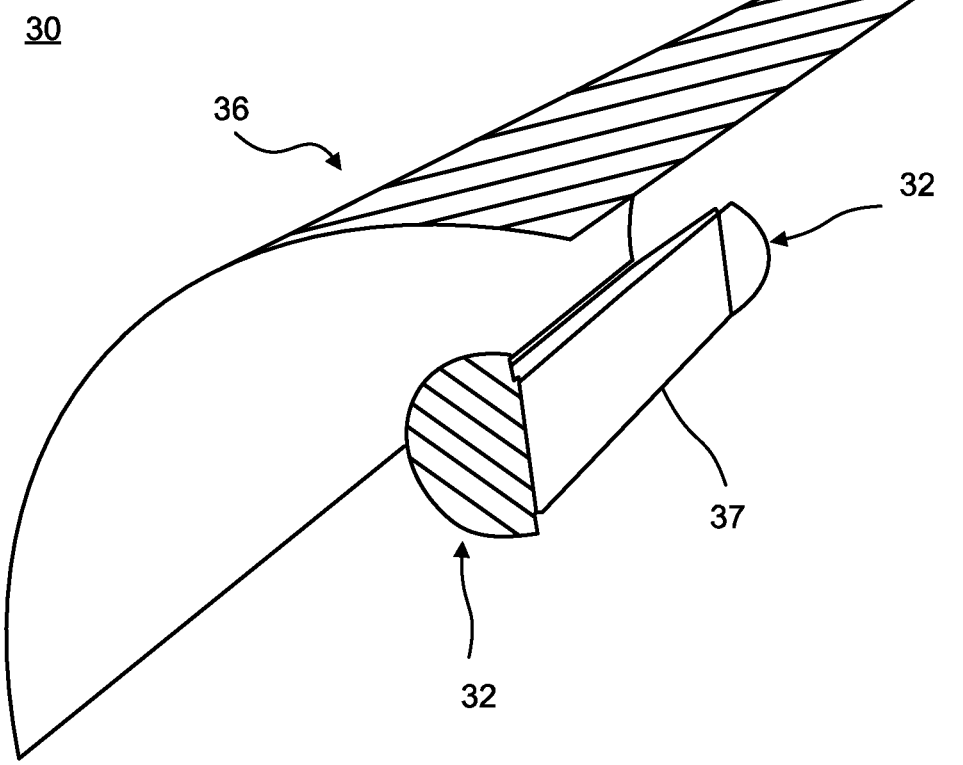
FIG. 10 is a three-quarters perspective view of the flexible circuit board of FIG. 9 in a semi-folded configuration.

FIG. 10 is a three-quarters perspective view of the flexible circuit board 30 of FIG. 9 in a semi-folded configuration. When placed within the central tubular body, the flexible circuit board 30 forms three aspects 31 of a microcontroller circuit assembly that respectively define a receiving coil 36 for energy capture, a pair of inter-device connecting ears 32, and a printed circuit board 37 containing a low power microcontroller and device circuitry operable to execute under modular micro program control as specified in firmware. The flexible circuit board 30 can be folded into a triangular shape or horseshoe shape (not shown) and each of the inter-device connecting ears 32 are folded angularly inward towards the triangular ends of the triangular shape 34. The foldable area 33 is either folded or rolled around the triangular shape of the flexible circuit board 30 and ears 32. Other shapes may be possible, including other variations on "ears" or extensions to the flexible circuit board 30.

Receiving Coil

A power receiving coil 36 is formed by folding (or rolling) the foldable (or rollable) area 33 (shown in FIG. 9) circumferentially about the triangular or horseshoe shape that contains the microcontroller and device circuitry. The foldable (or rollable) area 33, however, is longer than the flexible circuit board 30 and is defined, when installed inside the IMD 10, to extend for substantially the entire longitudinal length of the tubular body 11. The receiving coil 36 uses planar trace construction to maximize the capture of magnetic flux and provides insulation between the positive and negative electrode poles of the IMD 10. In further embodiments, signals can be routed from the spherical end caps through the antenna. As well, additional sensors can be implanted in the antennas.

In one embodiment, the receiving coil 36 that is used for gathering energy to recharge the power source is connected to a clamping diode array and fusible link. In the presence of extreme electromagnetic environments, the protection diode array will limit the voltage across the antenna protecting the device charging circuitry. If the diode array is overwhelmed for a long enough period of time, the fusible link will open to protect the patient from the effects of device heating due to excessive charging energy received from the receiving coil. The fusible link may optionally be constructed out of a resettable overcurrent device, thermally actuated device, or fusible current limiting device.

In a further embodiment, the foldable (or rollable) area 33 is defined to form, when installed inside the IMD 10, a diagonal antenna that (not shown) will limit dead zones by creating a spiral where the two halves of the receiving coil connect. A standard square-shaped receiving coil could potentially lead to an RF dead zone in certain orientations. The diagonal antenna has a wide track and is overlaid, so that there are two overlapping areas, which should result in efficient flux capture for fields passing through the antenna.

In one embodiment, the high frequency antenna, when formed on a foldable ear 32 of the flexible circuit board 30, can be folded in different ways to create a range of antenna shapes. Note that more than one high frequency antenna could be used. The antenna is completely integrated into the flex circuit, which eliminates feedthrough that also translates into much better energy coupling.

In one embodiment, the receiving coil is sandwiched between the central tubular body 11, which can be a titanium cylindrical enclosure, and the case of the power source, described infra, which can also be a cylindrical titanium battery case. During inductive charging, eddy currents are induced in the titanium battery case. The eddy currents can raise the temperature of the IMD 10 and can reduce charge efficiency. This effect can be countered by reflecting the low frequency charging magnetic field into the low frequency energy receiving antenna with the increase in efficiency resulting in less heating. A ferrite coating or ferrite sheet can be applied to the outside casing of the power source to increase charge transfer efficiency by reflecting energy back into the receiving coil. Since the energy is reflected, less heating of the power source will occur during inductive charging due to decreased eddy currents.

Forming the power receiving coil 36 by folding or rolling the flexible circuit board provides several benefits over conventional implantable device design. First, the folding or rolling of the flexible circuit board affords a thin design that facilitates patient comfort by enabling compact packaging, resulting in an smaller device than would otherwise be available in a comparably rechargeable design. Second, the wide aspect ratio of the power receiving coil, when compared with to a traditional wire coil, allows a low loss element, thereby decreasing device heating. Moreover, the low loss element enables quicker charging through higher energy reception without excessive heating. Third, the unique shape enables injectable implantation technique that are not possible with traditional planar coils. Finally, the completely integrated design of the printed circuit board containing the microcontroller and related circuitry and the receiving coil simplifies device design, decreases weight, improves device longevity, and increases patient safety by virtue of requiring fewer parts and no discrete interconnections using, for instance, soldered wires or circuit traces.

Power Source and Charging Circuit

A power source that includes an inductively-rechargeable energy cell, battery, or supercapacitor is also placed within the IMD 10 to one end of the flexible circuit board 30 and in electrical contact with the electrically conductive semi spherical end cap 13, thereby serving as an electrical feedthrough to the flexible circuit board 30. The power source may be recharged through a charging and conditioning circuit interfaced with the microcontroller using a non-contact method, such as inductive charging, resonant charging, energy harvesting, thermal gradient charging, ultrasonic charging, RF-based charging or charging by ambient or driven motion including vibration. Low frequency charging circuits are most efficient at transmitting energy through solid objects. When a charging circuit operates, vibrations are induced in the coils used in the charger as well as surrounding conductive objects. However, these vibrations, if within the human audible hearing range (or a close multiple thereof) create sound.

A traditional charging circuit uses a single frequency to transmit power. If the frequency or a major harmonic thereof is within the audible human hearing range, a single tone that humans can find very annoying could result. To overcome this issue, traditional charging circuits operate above the human audible hearing range. However, instead of using a single frequency for charging, a low frequency charging circuit could also modulate the charging waveform at audible frequencies that result in a pleasant sound for the user, so as to allow the technical benefits of low frequency charging without causing annoyance to humans.

Modulation of frequencies requires receive and transmit circuitry with higher bandwidth to accommodate the frequency shifts efficiently. The modulation can cause decreased circuit Q ("quality"), which can be overcome by using a variable capacitor or other automatic tuning circuit to ensure sufficient resonance as the frequency changes. For example, if the frequency changes, tuning may be required to restore satisfactory coupling. The automatic tuner circuit could predict the value needed to achieve resonance or a high Q factor based on the input frequency, or alternatively could employ a feedback system to self-tune as the input frequency changes. The automatic tuner circuit could further be employed to efficaciously control charging to decrease overall charging time. Differences in devices, patients and their environment will modify the Q factor of the system. An automatic turning circuit can automatically compensate for these changes.

In a still further embodiment, a feedback circuit or system could be further employed to automatically compensate for changes in the environment and patient load. The feedback circuit would tune charging based on input energy. Alternatively, the feedback circuit method is to know what is coming and instantly auto tune the charging circuitry based on the pattern that will be sent shortly to the IMD 10.

The feedback system could also be used to provide positive feedback to the patient. For instance, the modulation frequency could produce a very "futuristic" sound, such as a low to high frequency ramp, which repeats at a predetermined interval, or could even play a song, perhaps of the patient's choosing. Further, the modulation frequency could be used to signal to the user the state of the device, such as charging, error condition, or completion of charging.

Encasement

The power source may optionally be encased in a metallic cylindrical case that also functions as an electrical feedthrough, where the outside of the power source case is used as a conductor to the electrode connection. Conventional IMDs are typically rectangular or prismatic in shape. A cylindrical shape offer several advantages, including patient comfort, power source design, accommodations for different types of antennae, and improved insertability and ease of explant.

The actual electrode contact area forms a hollow dome to absorb any swelling that might occur during the extremely unlikely event of a catastrophic power source failure. A set of feedthroughs, arranged in a possible pattern of [+/Temp/−/chassis] is provided to provide increased safety, reduction of leakage currents and ease of assembly.

In one embodiment, the power source case is electro polished to improve the ability of the receiving coil 36 to slide over the power source case during installation. In a further embodiment, the head of the power source, that is, the end of the power source that faces outwards away from the flexible circuit board 30 and replaces the "Protectrode" assembly. The head is formed of thin titanium and shaped as a dome to serve as an electrode and provide internal relief for power source expansion if a failure occurs.

Chemistry

In one embodiment, the power source can use lithium titanate (LTO) technology. Alternatively, other power source or battery technologies such as Lithium Cobalt Oxide, Lithium Manganese Oxide, Lithium Nickel Manganese Cobalt Oxide, Lithium Iron Phosphate, Lithium Nickel Cobalt Aluminum Oxide, Nickel Cadmium or Nickel Meta Hydrate could be employed.

To accommodate complete discharge without oxidation of the power source collector, the copper collector typically found in a power source could be replaced by a corrosion resistant metal, such as stainless steel, titanium, gold or platinum. Furthermore, a collector could be made of a standard base metal and plated to increase corrosion resistance. This combination of materials could be copper, nickel, palladium, gold or titanium, gold, or stainless steel, gold or any appropriate combination thereof to provide the necessary degree of corrosion resistance and zero volt life. The surfaces of the materials and platings could be roughened to increase surface area and provide better charge and discharge characteristics.

Scalloped Electrodes

Figure 11:
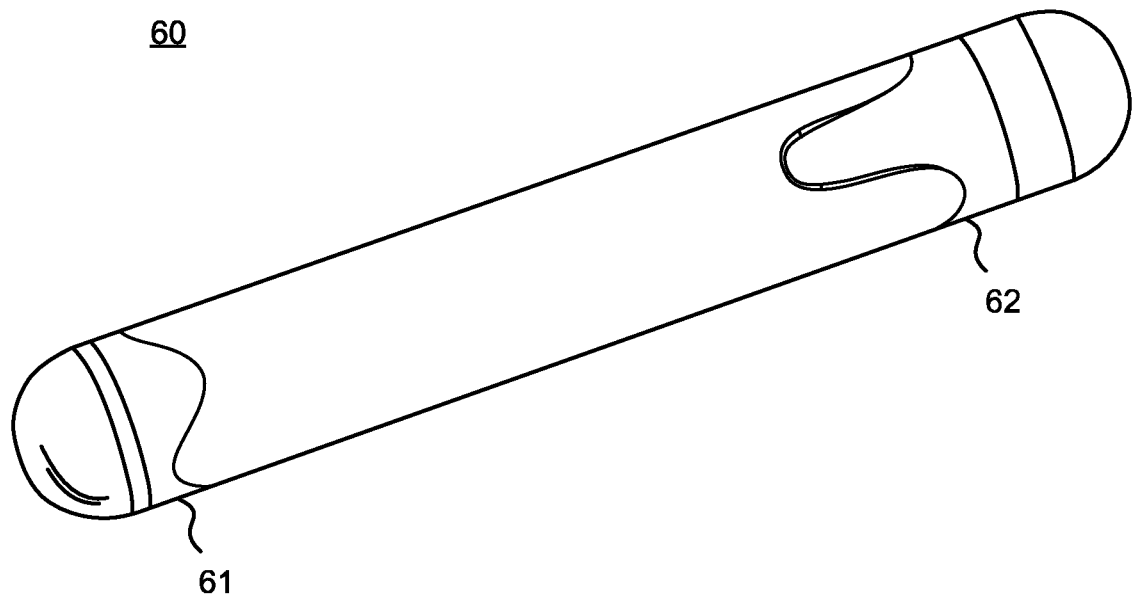
FIG. 11 is an outer perspective view showing an IMD that houses a configurable hardware platform for physiological monitoring of a living body in accordance with a further embodiment.

The proximity of the high frequency antenna 34 to the conductive surface 18 exposed on the outside surface of the tubular body 11 can, in some circumstances, pose a risk of ECG signal degradation. FIG. 11 is an outer perspective view showing an IMD 60 that houses a configurable hardware platform for physiological monitoring of a living body in accordance with a further embodiment. The electrode 61 formed as part of the "Protectrode" section of the IMD 60 and the electrode 62 formed on the outer surface of the tubular body 11 are shaped with scalloped cutouts on their respective inward facing aspects. The electrode formation minimizes potential parasitic coupling of the electrodes 61 and 62 to ground strips that are used for the high frequency antenna return. In addition, the shape of the "Protectrode" electrode 61 increases the performance and durability of the ceramic to titanium weld joints, when used, to join the "Protectrode" 12 to the tubular body 11.

Microarchitecture

The operation of the IMD 10, including data capture, analysis, and communication, is controlled by a programmable microcontroller. FIG. 12 is a block diagram showing the microarchitecture 40 of the IMD 10. The microcontroller is remotely interfaceable over a wireless radio frequency (RF) data communications link using the high frequency antenna 34 that is housed within the "Protectrode" 12, which enables the IMD 10 to provide continuous heartbeat-by-heartbeat monitoring and to be remotely reconfigured or reprogrammed to utilize one or more of the physiological sensors.

Microcontroller

In one embodiment, a low power, high efficiency microcontroller 41, such as a microcontroller from the RL78 family of microcontrollers offered by Renesas Electronics Corp., Tokyo, Japan, can be used. Architecturally, the microcontroller is built around a Harvard architecture that physically separates signal and storage pathways for instructions and data storage. The microcontroller operates under a dedicated microprogram stored as microcode within a nonvolatile memory device, rather than a general purpose operating system, which aids in efficient operation and longer power source life, although in a further embodiment, an operating system including a real time operating system, could be used. Note that there is memory located on the microcontroller as well as externally and program instructions are expected to be stored in the microcontroller's flash memory.

Additional Components

The microcontroller 41 is interfaced to components, both integrated and off-chip, that provide continuous and extensible monitoring capabilities to the IMD 10. A voltage regulation/charge control circuit 48 is interfaced to the low frequency resonant charger antenna 47 and the microcontroller 41, which together regulate and control the charging of the power source 49. An integrated Bluetooth system-on-a-chip (SoC) transceiver circuit 42 is similarly interfaced to the high frequency antenna 34 and the microcontroller 41 to provide data communications capabilities to the IMD 10. An electrode dipole is formed by electrodes 45 and 46, which are interfaced to an analog front end (AFE) 44 and to the microcontroller 41 to effect electrocardiographic monitoring. In one embodiment, temperature, actigraphy, and motion sensing are respectively provided through a temperature sensor 50, Hall effect switch 51, and accelerometer 52. Finally, monitoring data, including continuous ECG data awaiting offloading, are stored in mass storage 53 in the form of random access memory.

Paradigm

Purpose-build IMDs, such as implantable cardiac monitors (ICMs), are specifically designed to address a range of potential conditions which would be observable over an expected patient population. Thus, typical ICMs require power hungry and complex signal filters, which are able to detect R-wave intervals on a very high percentage of the patient population. Practically, however, the majority of the patient population does not need extreme filtering. As a result, dramatic power savings are possible if a signal filter could be selected that is appropriate for a given patient and for patients with special needs, strong signal filtering can be selected to reduce false positives at the cost of high power consumption and frequent recharging.

Here, the IMD 10 implements a configurable hardware platform based on a reprogrammable microcontroller that can be supplemented with additional physiological sensors, including an $SpO_2$ sensor, a blood pressure sensor, a temperature sensor, respiratory rate sensor, a glucose sensor, an air flow sensor, and a volumetric pressure sensor, and non-physiological sensors, including an accelerometer and inertial motion sensor. Through the microcontroller 41, the sensors can be selectively activated over the implantation lifetime, whether in real time or during reprogramming, to tailor the monitoring of the patient to ongoing diagnostic needs.

The microcontroller-based design also affords the flexibility to choose signal filtering and processing algorithm options tailored to each patient. This microarchitecture allows the best patient experience by eliminating designs that adopt a one-size-fits-all approach and which are dominated by considerations of accommodating the hardest cases. The microarchitecture further accommodates changes to patient morphology; modifications to the filtering software can be selected dynamically and updated in the field as a configuration update that is pushed by a physician from the "cloud," that is, the server paradigm that virtualizes server-side functionality as a service widely available through access to the internet or other wide-area data communications network.

In a further embodiment, the transceiver 42 can be used in conjunction with the microcontroller to communicate with ingestible sensors, such as offered by Proteus Digital Health, Inc., Redwood City, Calif. Ingestible sensors are pills made of biocompatible materials, which combine remote monitoring microelectronics with medication or inert materials that can safely be taken by a patient. Typically, an ingestible sensor is activated by gastric fluids dissolving or acting upon its surface, after which the sensor begins to measure gastro-intestinal tract physiology and, possibly, other types of physiology. Ingestible sensors that are capable of communicating wirelessly, such as over Bluetooth, Medradio, or via WiFi, are available as a real-time-capable alternative to standalone ingestible sensors that store recorded physiology onboard the device. This wireless-capable class of ingestible sensors allows the sensory data to be captured in real time. Moreover, these types of ingestible sensors aAcan be coupled with the IMD 10; thus, a patient can be monitored for medication compliance by providing accurate, time-correlated data that can be used to evaluate non-adherence and to provide positive reinforcement. The patient's caregiver can be notified in real time as to a patient's behavior with respect to adhering to prescribed medication.

The platform described facilitates the monitoring of every heartbeat in contrast to conventional non-rechargeable platforms, which typically do not have enough power to store and transmit each heartbeat. In addition to monitoring each heartbeat, since the heartbeats are offloaded, the heartbeats may be analyzed by an intelligent algorithm not located in the platform proper, which allows for better recognition of arrhythmias and disease conditions, as the complexity of the algorithm is not limited by the amount of power available to the analyzing device.

The IMD 10 continuously monitors the patient's heart rate on a heartbeat-by-heartbeat basis and physiology. FIG. 13 is a flow diagram showing a method 100 for continuously monitoring electrocardiography for use in the IMD 10 of FIG. 1. Initially, following successful implantation, the microcontroller 41 executes a power up sequence (step 101). During the power up sequence, the voltage of the power source 49 is checked, the state of the mass storage (flash memory) 53 is confirmed, both in terms of operability check and available capacity, and microcontroller operation is diagnostically confirmed.

Following satisfactory completion of the power up sequence, an iterative processing loop (steps 102-114) is continually executed by the microcontroller 41. During each iteration (step 102) of the processing loop, the AFE 44, through the electrode dipole created by electrodes 45 and 46, continually senses electrocardiographic signals; additionally, patient physiology is sampled at appropriate intervals, depending upon the sampling frequency selected for the particular type of physiology being sensed (step 103). One or more types of physiology can be sensed at any given time. The type and sampling rate of physiology are selectively activated over the lifetime of the IMD 10 via the microcontroller 41 through programmatic control, which in turn, determines the hardware device being utilized. For instance, reading patient temperature once each minute would require activation of the temperature sensor 50. A similar approach to sensing non-physiological data, such as position or posture, is followed mutatis mutandis.

A sample of the ECG signal and, at appropriate intervals, physiology, are read (step 104) by the microcontroller 41 by sampling the AFE 44 and appropriate physiology sensing hardware. Each sampled ECG signal and each of the physiology signals, in quantized and digitized form, are temporarily staged in a buffer (step 105), pending compression preparatory to storage in the mass storage 53 (step 106). Following compression, the compressed ECG digitized samples are again buffered (step 107), then written to the mass storage 53 (step 108) using the communications bus. Processing continues (step 114), so long as storage space remains available in the mass storage 53, after which the processing loop is exited. Still other operations and steps are possible.

The IMD 10 processes sensing signals generated by ingestible sensors follow a similar methodology as with processing monitored physiology, with two important distinctions. First, ingestible sensors are typically activated upon ingestion and thereafter generate monitoring data only during the time in which they are present in the patient's digestive tract. Second, ingestible sensor data is generally time-sensitive, where the correlation of the time of signal generation and time of day is of notable interest in itself, whereas physiological data is typically seen in the context of other physiological events, such as $SpO_2$, which is significant with reference to cardiac events.

Concurrently, the IMD 10 can offload stored monitoring data to a datacenter or other external device. The data is offloaded in a conceptually-separate execution thread as part of the iterative processing loop (steps 102-114) continually executed by the microcontroller 41. If an offloading event occurs (step 109), the IMD 10 connects to a mobile device (step 110), such as a smart phone or cellular-enabled tablet, and the stored samples are sent from the mass storage 53 to the mobile device (step 111). In turn, the mobile device relays the uploaded ECG and physiology samples to the datacenter. Alternatively, the IMD 10 can connect directly to the datacenter, provided the transceiver 42 is sufficiently capable. The mass storage 53 is cleared (step 112) and the IMD 10 disconnects from the mobile device (step 113) upon completion of the sending of the stored samples. Processing continues (step 114). Still other operations and steps are possible.

While the invention has been particularly shown and described as referenced to the embodiments thereof, those skilled in the art will understand that the foregoing and other changes in form and detail may be made therein without departing from the spirit and scope.

What is claimed is:

1. An implantable medical device (IMD), comprising:
    a housing comprising a hollow body forming a first sensing electrode on an outer surface of the hollow body with end caps affixed to opposite ends of the hollow body, one such end cap comprising an electrically conductive semi sphere that serves as a second sensing, electrode, a second one of the end caps comprising an antenna, the first sensing electrode comprising an electrically conductive surface that is an integral part of a portion of the outer surface of the hollow body and that is separated from the one end cap by an electrically insulating surface treatment applied to a further portion of the outer surface of the hollow body, wherein the first sensing electrode is located at one of the ends of the hollow body and interfaces to the second end cap comprising the antenna, and wherein the further portion of the outer surface of the hollow body covered by the electrically insulating surface treatment is larger than the portion of the outer surface of the hollow body that comprises the electrically conductive surface; and
    a microcontroller circuit circumferentially provided within the housing and comprising a microcontroller operable under program instructions stored within a non-volatile memory device comprised in the microcontroller, further comprising:
    an analog front end electrically interfaced to the first and the second sensing electrodes and operable to sense electrocardiographic signals via the first and the second sensing electrodes;
    a transceiver circuit operable to wirelessly communicate with an external data device via the antenna;
    the program instructions defining instructions for the microcontroller to continuously sample the electrocardiographic signals into a further memory and to offload the further memory to the external data device via the transceiver circuit;
    a receiving coil and a charging circuit are operable to charge an onboard power source for the microcontroller circuit; and
    the further memory.

2. An IMD in accordance with claim 1, further comprising:
    a physiological sensor other than the first and second sensing electrodes operable to sense physiological data other than the electrocardiographic signals sensed via the first and second sensing electrodes; and
    the program instructions defining instructions for the microcontroller to sample the physiological data at set times into the further memory.

3. An IMD in accordance with claim 1, further comprising:
    the transceiver circuit configured to wirelessly communicate with a wireless ingestible sensor that is outside the housing and that is operable to provide physiological monitoring data while within a patient; and
    the program instructions defining instructions for the microcontroller to receive the physiological monitoring data via the transceiver circuit and to store the received physiological monitoring data into the further memory.

4. An IMD in accordance with claim 1, further comprising:
    the onboard power source interposed between the microcontroller circuit and the one such end cap, the onboard power source comprising an electrically conductive outer surface through which the second electrode interfaces to the analog front end.

5. An implantable medical device (IMD), comprising:
    a cylindrical hollow body forming a first sensing electrode on an outer surface of the hollow body;
    a first spherical end cap attached on one end of the hollow body;
    a second spherical end cap attached on another end of the hollow body and comprising an electrically conductive semi sphere that serves as a second sensing electrode on an outer surface of the second spherical end cap, the first sensing electrode comprising an electrically conductive surface that is an integral part of a portion of the outer surface of the hollow body and that is separated from the second end spherical cap by an electrically insulating coating with which a further integral portion of the outer surface of the hollow body is treated, wherein the electrically conductive surface is located at the one end of the hollow body and interfaces to the first spherical end cap, and wherein the further integral portion of the outer surface of the hollow body covered by the electrically insulating coating is larger than the integral part of the portion of the outer surface of the hollow body that comprises the electrically conductive surface; and
    electronic circuitry housed within the hollow body, comprising:
    a microcontroller operable under program instructions contained in microcode stored within a non-volatile memory device comprised in the microcontroller;
    a physiological sensor separate from the electrodes operable to sense physiological data different than electrocardiographic signals and electrically interfaced to the microcontroller;
    an analog front end electrically interfaced to the first and the second sensing electrodes and the microcontroller and operable to sense electrocardiographic signals via the first and second sensing electrodes;
    a transceiver circuit electrically interfaced to a high frequency antenna that is housed within the first spherical end cap and to the microcontroller and operable to wireles sly communicate with an external data device;
    a receiving coil formed as part of a non-contact charging circuit;
    the program instructions operable to instruct the microcontroller to continuously sample the electrocardiographic signals and the physiological data at set times into a further memory and to offload the further memory to the external data device via the transceiver circuit; and
    the further memory; and
    a power source housed within the hollow body and electrically interfaced to the non-contact charging circuit, the power source operable to power the microcontroller, the power source comprising an electrically conductive outer surface through which the second electrode interfaces to the analog front end.

6. An IMD in accordance with claim 5, the IMD further comprising:
a further physiological sensor different from the physiological sensor, the first sensing electrode, and the second sensing electrode, and operable to sense further physiological data different from the physiological data sensed by the physiological sensor and the electrocardiographic signals, the further physiological sensor electrically interfaced to the microcontroller; and
the program instructions defining instructions for the microcontroller to selectively activate at least one of the physiological sensor and the further physiological sensor.

7. An IMD in accordance with claim 5, further comprising:
the transceiver circuit configured to wirelessly communicate with a wireless ingestible sensor that is outside the hollow body and that is operable to provide physiological monitoring data sensed while activated within the digestive tract, wherein the physiological monitoring data is different from the physiological data and the electrocardiographic signals; and
the program instructions defining instructions for the microcontroller to receive the physiological monitoring data via the transceiver circuit during activation of the wireless ingestible sensor and to store the received physiological monitoring data into the further memory.

8. An IMB in accordance with claim 5, further comprising:
the receiving coil adapted to be circumferentially disposed about the electronic circuitry within the hollow body.

9. An implantable medical device (IMD), comprising:
a main cylindrical body defining an axial bore extending longitudinally over the length of the main cylindrical body and exposing an electrically conductive area defining a first sensing electrode, wherein the electrically conductive area is an integral part of an outer surface of the main cylindrical body;
a spherical end cap fixedly disposed on one end of the main cylindrical body and defining an interior cavity, the spherical end cap exposing a further electrically conductive area that defines an electrically conductive semi sphere defining a second sensing electrode on at least a part of an outer surface of the spherical end cap, wherein the electrically conductive area defining the first sensing electrode is separated from the spherical end cap by an electrically insulating coating with which a further integral part of the outer surface of the main cylindrical body is treated, wherein the electrically conductive surface is located at an end of the main cylindrical body and is interfaced to an antenna spherical end cap, and wherein the further integral part of the outer surface of the main cylindrical body covered by the electrically insulating coating is larger than the integral part of the outer surface of the main cylindrical body that comprises the electrically conductive area;
the antenna spherical end cap fixedly disposed on one end of the main cylindrical body and defining an interior cavity with a high frequency antenna housed within; and
a printed circuit board housed within the main cylindrical body, comprising: electronic circuitry, comprising:
a physiological sensor other than the first and second sensing electrodes operable to sense physiological data other than electrocardiographic signals sensed via the first and second sensing electrodes;
an analog front end electrically interfaced to the first and the second sensing electrodes and operable to sense electrocardiographic signals via the first and second sensing electrodes;
a transceiver circuit electrically interfaced to the high frequency antenna and operable to wirelessly communicate with an external data device; and
a microcontroller that is operable under program instructions contained in microcode stored within a non-volatile memory device within the microcontroller and electrically interfaced with the physiological sensor, the analog front end, and the transceiver circuit, the microcontroller operable under the program instructions to record the physiological data at set times and the electrocardiographic signals continuously into a further memory and to offload the electrocardiographic signals from the further memory to the external data device;
a receiving coil formed on an extended surface of the printed circuit board that is adapted to be circumferentially disposed about the electronic circuitry and provided as part of a non-contact charging circuit; and
the further memory; and
a power source comprising a rechargeable energy cell housed within the main cylindrical body and electrically interfaced with the charging circuit, the power source operable to power the electronic circuitry.

10. An IMD in accordance with claim 9, further comprising:
the transceiver circuit configured to wirelessly communicate with a further physiological sensor operable to be activated upon ingestion, after which the ingested further physiological sensors transmits physiological monitoring data different from the physiological data sensed by the physiological sensor,
wherein the microcontroller is operable under the program instructions to selectively activate at least one of the physiological sensor and the further physiological sensor and to store the received physiological monitoring data into the further memory.

11. An IMD in accordance with claim 10, further comprising one of:
one of a plurality of connecting ears being vertically disposed within the housing relative to the printed circuit board and electrically interposed between the high frequency antenna and the transceiver circuit; and
one of the plurality of connecting ears being vertically disposed within the housing relative to the printed circuit board, wherein the high frequency antenna electrically interfaced to the transceiver circuit is formed on that connecting ear.

12. An IMD in accordance with claim 11, further comprising:
another one of the plurality of connecting ears being vertically disposed within the housing relative to the electronic circuitry and electrically connects the analog front end and the second sensing electrode and the charging circuit and the power source.

13. An IMD in accordance with claim 9, further comprising:
the transceiver circuit configured to wirelessly communicate with an ingestible sensor that is outside the main cylindrical body and that is operable to be activated upon ingestion, after which the ingestible sensor transmits physiological monitoring data, the physiological monitoring data different from the physiological data and the electrocardiographic signals;

wherein the microcontroller is operable under the program instructions to receive the physiological monitoring data via the transceiver circuit and to store the received physiological monitoring data into the further memory.

14. An IMD in accordance with claim 9, the printed circuit board further comprising:
   a first aspect forming a central tri-folded section upon which the electronic circuitry is comprised;
   a second aspect forming two connecting ears respectively defined on opposite ends of the first aspect; and
   a third aspect forming the receiving coil.

15. An 1MB in accordance with claim 9, wherein the power source is housed between the printed circuit board and the spherical end cap, an outer surface of the rechargeable energy cell being electrically communicative with the analog front end.

16. An IMD in accordance with claim 9, wherein the physiological sensor is selected from the group comprising an $SpO_2$ sensor, a blood pressure sensor, a temperature sensor, respiratory rate sensor, a glucose sensor, an air flow sensor, and a volumetric pressure sensor.

17. An IMD in accordance with claim 9, the IMB further comprising a non-physiological monitor selected from the group comprising an actigraphy sensor, accelerometer, and inertial motion sensor.

* * * * *

UNITED STATES PATENT AND TRADEMARK OFFICE
CERTIFICATE OF CORRECTION

PATENT NO. : 11,696,681 B2
APPLICATION NO. : 16/929390
DATED : July 11, 2023
INVENTOR(S) : Jason Felix et al.

It is certified that error appears in the above-identified patent and that said Letters Patent is hereby corrected as shown below:

In the Claims

Please delete "wireles sly" in Column 18, Line 55 and insert --wirelessly--

Please delete "IMB" in Column 19, Line 32 and insert --IMD--

Please delete "1MB" in Column 21, Line 17 and insert --IMD--

Please delete "IMB" in Column 21, Line 27 and insert --IMD--

Signed and Sealed this
Fifth Day of September, 2023

Katherine Kelly Vidal
*Director of the United States Patent and Trademark Office*